US012106842B2

(12) United States Patent
Avery et al.

(10) Patent No.: US 12,106,842 B2
(45) Date of Patent: Oct. 1, 2024

(54) SYSTEMS, METHODS, AND MEDIA FOR AUTOMATED DIETARY MANAGEMENT IN HEALTHCARE FACILITIES

(71) Applicant: Direct Supply, Inc., Milwaukee, WI (US)

(72) Inventors: William L. Avery, West Chicago, IL (US); Andrew J. Novotny, Whitefish Bay, WI (US); Meagan E. Harrison, Denver, CO (US); Nathanial C. Ziarek, Muskego, WI (US); Ryan G. Colwell, West Bend, WI (US); Anne F. B. Dorn, Fox Point, WI (US)

(73) Assignee: Direct Supply, Inc., Milwaukee, WI (US)

( * ) Notice: Subject to any disclaimer, the term of this patent is extended or adjusted under 35 U.S.C. 154(b) by 729 days.

(21) Appl. No.: 17/163,913

(22) Filed: Feb. 1, 2021

(65) Prior Publication Data

US 2021/0241881 A1    Aug. 5, 2021

Related U.S. Application Data

(60) Provisional application No. 62/968,793, filed on Jan. 31, 2020.

(51) Int. Cl.
G16H 20/60    (2018.01)
G16H 10/60    (2018.01)
G16H 40/67    (2018.01)

(52) U.S. Cl.
CPC .............. *G16H 20/60* (2018.01); *G16H 10/60* (2018.01); *G16H 40/67* (2018.01)

(58) Field of Classification Search
CPC ........ G16H 20/60; G16H 10/60; G16H 40/67; G16H 50/70
See application file for complete search history.

(56) References Cited

U.S. PATENT DOCUMENTS

| | | | |
|---|---|---|---|
| 6,370,513 | B1 | 4/2002 | Kolawa et al. |
| 8,504,440 | B1 | 8/2013 | Kolawa et al. |
| 9,424,495 | B1 | 8/2016 | Trevino |
| 9,489,377 | B1 | 11/2016 | Feller et al. |
| 9,536,052 | B2 | 1/2017 | Amarasingham et al. |
| 9,558,515 | B2 | 1/2017 | Babu et al. |
| 9,785,983 | B2 | 10/2017 | Zhao et al. |
| 9,797,873 | B1 | 10/2017 | Feller et al. |
| 10,013,569 | B2 | 7/2018 | Wu et al. |
| 10,255,455 | B2 | 4/2019 | Casse |
| 10,282,512 | B2 | 5/2019 | Bennett et al. |
| 10,331,490 | B2 | 6/2019 | Leonard et al. |

(Continued)

OTHER PUBLICATIONS

The Academy Quality Management Committee, Academy of Nutrition and Dietetics: Scope of Practice for the Registered Dietitian, Journal of The Academy of Nutrition and Dietetics, 2013, 113(6):S17-S28.

(Continued)

*Primary Examiner* — Apu M Mofiz
*Assistant Examiner* — Oscar Wehovz
(74) *Attorney, Agent, or Firm* — Quarles & Brady LLP

(57) ABSTRACT

In accordance with some embodiments of the disclosed subject matter, mechanisms (which can, for example, include systems, methods, and media) for automated dietary management in healthcare facilities are provided.

20 Claims, 19 Drawing Sheets

(56) References Cited

U.S. PATENT DOCUMENTS

| | | | |
|---|---|---|---|
| 10,352,759 B1 | 7/2019 | Jensen | |
| 2003/0059747 A1 | 3/2003 | Yoshida et al. | |
| 2004/0078225 A1* | 4/2004 | Schramm-Apple | G09B 5/00 |
| | | | 705/2 |
| 2006/0199155 A1* | 9/2006 | Mosher | G16H 20/60 |
| | | | 434/127 |
| 2009/0271293 A1 | 10/2009 | Parkhurst et al. | |
| 2013/0262357 A1 | 10/2013 | Amarasingham et al. | |
| 2013/0304492 A1* | 11/2013 | Hermann | G16H 20/40 |
| | | | 705/2 |
| 2014/0142966 A1* | 5/2014 | Badgett | G06Q 10/06 |
| | | | 705/2 |
| 2015/0019241 A1 | 1/2015 | Bennett et al. | |
| 2016/0071432 A1 | 3/2016 | Kurowski et al. | |
| 2016/0117485 A1 | 4/2016 | Allen et al. | |
| 2016/0140318 A1 | 5/2016 | Stangel | |
| 2016/0171383 A1 | 6/2016 | Narain et al. | |
| 2016/0203287 A1 | 7/2016 | Chen et al. | |
| 2016/0242451 A1 | 8/2016 | Gillespie | |
| 2016/0253514 A1 | 9/2016 | Wu et al. | |
| 2016/0292391 A1 | 10/2016 | Fink et al. | |
| 2017/0052536 A1 | 2/2017 | Warner et al. | |
| 2017/0061093 A1 | 3/2017 | Amarasingham et al. | |
| 2017/0091391 A1 | 3/2017 | LePendu | |
| 2018/0122500 A1* | 5/2018 | Harrell Vines | G06F 21/6218 |
| 2019/0066849 A1 | 2/2019 | Lawrence et al. | |
| 2019/0214134 A1 | 7/2019 | Bates | |
| 2019/0243922 A1 | 8/2019 | Pinel et al. | |
| 2019/0304578 A1* | 10/2019 | Kain | G06F 16/2379 |
| 2019/0304582 A1 | 10/2019 | Blumenthal et al. | |
| 2019/0311790 A1 | 10/2019 | Dadkhahnikoo et al. | |
| 2021/0004715 A1* | 1/2021 | Neumann | G16H 15/00 |
| 2022/0084654 A1* | 3/2022 | Flaherty | G16H 20/60 |

OTHER PUBLICATIONS

Capgemini, Blockchain: A Healthcare Industry View, Copyright 2017 Capgemini, 16 pages.

Rajkomar et al., Scalable and Accurate Deep Learning with Electronic Health Records, NPJ Digital Medicine, 2018, 1:18, 10 pages.

Yoon, Blockchain Technology and Healthcare, Healthcare Informatics Research, 2019, 25(2):59-60.

* cited by examiner

Week 1 Day 1
Breakfast

| | Regular | Consistent C | Mech Soft | Pureed | Finger Fd | Fortified | Renal | 2gm Na |
|---|---|---|---|---|---|---|---|---|
| Juice of Choice | 6 flz | X | X | X | X | X | Cranberry Juice | X |
| Oatmeal | 6z ladle | X | X | #6 scoop Pureed Oatmeal | 3/4 cup Chc Ckd Crl | 6oz ladle Super Cereal | X | X |
| Cheese Omelet | 1 each | X | X | #12 scoop Pureed Cheese O | X | X | X | 1 Egg Choice of Egg |
| Bacon | 2 Slices | X | #16 scoop Sausage Link Gr | #16 Scoop Pureed Sausage | X | X | No | No |
| White Toast | 1 slice | half slice | X | 3"x3" Slice Pureed Bread | X | X | X | X |
| Whipped Butter Cup 5-8g | 1 each | X | X | X | X | X | X | X |
| Assorted Jam & Jelly | 1 Each | Diet Jelly | X | X | X | X | X | X |
| 2% White Milk | 8 flz | 8 Floz Skim Milk | 8 Floz | 8 Floz | 8 Floz | 8 Floz Whl Milk | X | 8 Floz |
| Hot Beverage | 8oz | X | X | X | X | X | X | X |

Lunch

| | Regular | Consistent C | Mech Soft | Pureed | Finger Fd | Fortified | Renal | 2gm Na |
|---|---|---|---|---|---|---|---|---|
| Pot Roast | 3z piece | X | #10 scp, 2flz gvy Ground Pot Roas | #10 scoop Pureed Pot Roas | X | X | X | X |
| Onion Roasted Potatoes | 4z spoodle | X | X | #8 scp, no skins Pureed Onion R | X | X | #10 scoop White Rice | 1 potato Baked Potato |
| Glazed Carrots | 4z spoodle | X | X | #12 scoop Pureed Glazed C | Buttered Baby C | X | X | X |
| Dinner Roll | 1 roll | No | X | #24 scoop Pureed Bread | 1 Each WG Ham Bun | X | X | No |
| Apple Pie | 1/8th slice | #8 scoop Hot Spiced Apple | X | #10 scoop Pureed Apple Pi | 1 cookie Sugar Cookie | X | #8 scoop Hot Spiced Appl | #8 scoop Hot Spiced Appl |
| Whipped Butter Cup 5-8g | 1 each | No | No | X | No | X | X | X |
| Sour Cream | No | No | No | No | No | No | No | Tablespoon |
| Mighty Milk 2 | No | No | No | No | No | 8oz Cup | No | No |
| Hot Beverage | 8oz | X | X | X | X | X | X | X |

Jane Doe

- [FACTOR A] and [FACTOR B] strongly indicate a move to [RESTRICTION]
- [FACTOR B] and [FACTOR C] strongly indicate a move to [RESTRICTION]

View Chart

John Doe

- [FACTOR A] and [FACTOR B] indicate a move to [RESTRICTION]

View Chart

Apply Recommendations

FIG. 18

▷ Facility A

▽ Facility B

Jane Doe No Change

John Doe Remove liquid restriction

Brian Doe Add renal dietary restriction

Peter Doe Unable to evaluate

Carey Doe Remove all restrictions

Ryan Doe Add carb control dietary restriction

▷ Facility C

▷ Facility D

▷ Facility E

FIG. 20

SYSTEMS, METHODS, AND MEDIA FOR AUTOMATED DIETARY MANAGEMENT IN HEALTHCARE FACILITIES

CROSS-REFERENCE TO RELATED APPLICATIONS

This application is based on, claims the benefit of, and claims priority to U.S. Provisional Patent Application No. 62/968,793, filed Jan. 31, 2020, which is hereby incorporated herein by reference in its entirety for all purposes.

BACKGROUND

Organizations (e.g., for profit businesses, non-profit organizations, government entities, and so on) that provide meals and/or care for residents, patients, and/or others (e.g., students) are often required to meet federal, state, and/or local regulatory requirements, such as meeting specific nutritional requirements. For example, in acute care settings, a diet manual is required under federal regulations promulgated by the Centers for Medicare and Medicaid Services (CMS) and a registered dietitian must generally approve the diet manual and certify that it meets the nutritional standards required by the regulations. In long-term care settings, CMS regulations are not as clear, but some state regulations explicitly require diet manuals. This leads to many long-term care providers requiring a registered dietitian sign off on a diet manual regardless of whether it is explicitly required as part of the facilities compliance efforts. For example, skilled nursing facilities are required to meet regulatory requirements that are enforced at the federal level by the Centers for Medicare and Medicaid Services (CMS). The regulations enforced by CMS require, among other things, that particular staffing level, nutritional adequacy, and dietary requirements be satisfied at each skilled nursing facility. As another example, skilled nursing facilities may be required to comply with state and/or local regulations (e.g., regulations that implement a licensing requirement). Failures to fully comply with such requirements can result in the organization being fined, receiving reduced reimbursement rates (e.g., from Medicare and/or Medicaid), losing its license, or other consequences.

Many organizations hire and/or consult with one or more registered dietitians in an effort to comply with regulatory requirements related to nutrition. The registered dietitian can participate in activities such as menu planning, evaluations of resident's diets, and evaluation of resident's progress to assist the organization in its compliance efforts. In many cases, a registered dietitian is responsible for a particular facility or facilities. The job of a registered dietitian in an acute or long-term care setting is often very challenging because they have a lot of different responsibilities that are very time consuming to manually execute. Expected responsibilities often include: patient assessments, developing and evaluating menus that provide a wide variety of nourishing, palatable, well-balanced diets that meet residents daily nutritional and special dietary needs, taking into consideration the preferences of each resident, developing individualized diets (e.g., medical nutrition therapy diets, diets that correspond to one or more therapeutic diets) as required, providing nutrition education for patients and staff, overseeing budgets, purchasing and operations of foodservice, and participating in overall care team for patients/residents. Registered dietitians often interface with many disjointed systems and manual processes that they have to reference and piece together to ensure they are performing their job successfully and in compliance with applicable federal, state, and local regulations.

Accordingly, systems, methods, and media for automated dietary management in healthcare facilities are desirable.

SUMMARY

In accordance with some embodiments of the disclosed subject matter, systems, methods, and media for automated dietary management in healthcare facilities are provided.

In accordance with some embodiments of the disclosed subject matter, a method for generating a medical nutrition therapy diet for a patient in a facility is provided, the method comprising: receiving, from a remote first computing device associated with a particular registered dietitian over a communication network, a request for identifying information associated with one or more patients associated with the facility requiring development of a medical nutrition therapy diet; in response to the request for identifying information associated with one or more patients requiring development of a medical nutrition therapy diet, causing the first computing device to present, via a user interface, identifying information associated with a plurality of patients requiring development of a medical nutrition therapy diet; receiving, from the first computing device, a request to present patient data associated with a first patient of the plurality of patients; retrieving, from a second computing device over the communication network, at least a portion of nutrition data associated with the first patient, including at least one previous medical nutrition therapy diet assigned with the first patient, and data indicative of a dietary restriction associated with the first patient; causing the first computing device to present, via the user interface, the at least one previous medical nutrition therapy diet; causing the first computing device to present, via the user interface, at least a portion of the data indicative of the dietary restriction associated with the first patient; prompting, via the user interface presented by the first computing device, the particular registered dietitian to review the at least one previous medical nutrition therapy diet, and the data indicative of the dietary restriction associated with the first patient; receiving, from the first computing device based on input provided via the user interface, updated dietary restriction information comprising instructions to assign the first patient to a first diet type; causing a model to identify a plurality of food item options available for the first patient based on the first diet type; causing the first computing device to present, via the user interface, at least a subset of the plurality of food item options available for the first patient based on the plurality of items identified by the model that satisfy one or more conditions associated with the first diet type and that correspond to ingredients stocked by the facility; causing the first computing device to present, via the user interface, nutritional information associated with at least the subset of the plurality of food items options including a first item and a second item; receiving, from the first computing device, a request to add a first item of the plurality of items to the medical nutrition therapy diet; receiving, from the first computing device, a request to add a second item of the plurality of items to the medical nutrition therapy diet; causing the first computing device to present, via the user interface, nutritional information associated with the first item and the second item; prompting, via the user interface presented by the first computing device, the particular registered dietitian to confirm that the medical nutrition therapy diet comprising the first item and the second item satisfies the first patient's updated dietary restrictions including requirements associated with the first diet type; receiving, from the first computing device, an indication that input was received via the user interface confirming that the medical nutrition therapy diet satisfies the first patient's updated dietary restrictions; in response to receiving confirmation that the medical nutrition therapy diet satisfies the first patient's updated dietary restrictions, recording an indication that the particular registered dietitian approved the medical nutrition therapy diet as satisfying the first patient's updated dietary restrictions; and causing the medical nutrition therapy diet to be transmitted to a food service system to cause one or more meals to be prepared for the first patient at the facility based on the medical nutrition therapy diet.

In some embodiments, the method further comprises associating each of the plurality of patients with the facility based on at least one of identifying information associated with the patient and metadata associated with the patient.

In some embodiments, the method further comprises: receiving identifying information associated with the particular registered dietitian; and receiving a request to associate the particular registered dietitian with an organization that operates the facility.

In some embodiments, the method further comprises: receiving facility privileges information indicating that the particular registered dietitian has been granted privileges to practice at the facility; receiving licensing information indicating one or more jurisdictions in which the particular registered dietitian is licensed to practice; and causing the facility privileges information and the licensing information to be stored in a data store.

In some embodiments, the method further comprises: determining, based on the stored licensing information, that the particular registered dietitian is licensed to practice in a jurisdiction that requires licensure; and causing the first computing device to present, via the user interface, a user interface element that conveys information indicative of the particular registered dietitian being permitted to develop the medical nutrition therapy diet for the first patient.

In some embodiments, the method further comprises: determining, based on the stored facility privileges information, that the particular registered dietitian has been granted privileges to practice in the facility; and in response to determining that the particular registered dietitian has been granted privileges to practice in the facility, causing the first computing device to present, via the user interface, the user interface element.

In some embodiments, the method further comprises: causing the first computing device to present, via the user interface, a plurality of user interface elements corresponding to the subset of the plurality of food item options that convey a recommended medical nutrition therapy diet for the first patient selected by the model.

In some embodiments, the model is a trained machine learning model that was trained to select food items that comply with one or more nutrition restrictions, including food preparation restrictions, using training data comprising past medical nutrition therapy diets associated with a multitude of patients, information indicative of a dietary restrictions for each of the multitude of patients, and outcomes for each of the multitude of patients.

In some embodiments, the method further comprises: receiving, from an electronic health record system, medical record data associated with the first patient; and causing the first computing device to present, via the user interface, a plurality of user interface elements that convey medical condition data for the first patient extracted from the medical record data.

In some embodiments, the method further comprises: receiving outcome data associated with the first patient; generating training data using the medical nutrition therapy diet, the updated dietary restriction information, and the outcome data associated with the first patient; associating the training data with anonymized identifying information; providing the training data and the anonymized identifying information to a third computing device associated with the trained machine learning model such that the trained machine learning model can be updated using the training data while ensuring that personally identifying information of the first patient is not disseminated.

In some embodiments, the method further comprises: causing the model to be updated based on the medical nutrition therapy diet.

In some embodiments, the outcome data associated with the first patient comprises data indicative of the first patient's weight at two or more points in time associated with the medical nutrition therapy diet.

In some embodiments, the outcome data associated with the first patient comprises data indicative of the first patient's blood glucose at two or more points in time associated with the medical nutrition therapy diet.

In some embodiments, retrieving at least a portion of the nutrition data associated with the first patient comprises querying a blockchain distributed ledger in which prior medical nutrition therapy diet associated with the first patient are recorded, and the method further comprises: receiving patient data associated with the first patient, the patient data comprising at least any currently existing dietary restrictions, texture restrictions, liquid restrictions, likes, dislikes, patient feedback, allergies, and physician ordered restrictions recorded in an electronic health record associated with the patient; causing the patient data to be collected into a transaction data register; receiving data from the first computing device that was provided as input via the user interface; causing the data provided as input via the user interface to be collected into the transaction data register; receiving data from the model; causing the data received from the model to be collected into the transaction data register; causing the transaction register data to be configured into a new blockchain distributed ledger block; associating a cryptographic hash of a previous blockchain distributed ledger block and a timestamp with the new blockchain distributed ledger block; and causing the new blockchain distributed ledger block to be written to the blockchain distributed ledger using the cryptographic hash.

In accordance with some embodiments of the disclosed subject matter, a system for automatically generating a medical nutrition therapy diet order for a patient in a facility associated with an organization is provided, the system comprising: at least one hardware processor that is programmed to: receive, from a remote first computing device associated with a particular registered dietitian over a communication network, a request for identifying information associated with one or more patients associated with the facility requiring development of a medical nutrition therapy diet; in response to the request for identifying information associated with one or more patients requiring development of a medical nutrition therapy diet, cause the first computing device to present, via a user interface, identifying information associated with a plurality of patients requiring development of a medical nutrition therapy diet; receive, from the first computing device, a request to present patient data associated with a first patient of the plurality of patients; retrieve, from a second computing device over the communication network, at least a portion of nutrition data associated with the first patient, including at least one previous medical nutrition therapy diet assigned with the first patient, and data indicative of a dietary restriction associated with the first patient; causing the first computing device to present, via the user interface, the at least one previous medical nutrition therapy diet; causing the first computing device to present, via the user interface, at least a portion of the data indicative of the dietary restriction associated with the first patient; prompting, via the user interface presented by the first computing device, the particular registered dietitian to review the at least one previous medical nutrition therapy diet, and the data indicative of the dietary restriction associated with the first patient; receiving, from the first computing device based on input provided via the user interface, updated dietary restriction information comprising instructions to assign the first patient to a first diet type; causing a model to identify a plurality of food item options available for the first patient based on the first diet type; causing the first computing device to present, via the user interface, at least a subset of the plurality of food item options available for the first patient based on the plurality of items identified by the model that satisfy one or more conditions associated with the first diet type and that correspond to ingredients stocked by the facility; causing the first computing device to present, via the user interface, nutritional information associated with at least the subset of the plurality of food items options including a first item and a second item; receiving, from the first computing device, a request to add a first item of the plurality of items to the medical nutrition therapy diet; receiving, from the first computing device, a request to add a second item of the plurality of items to the medical nutrition therapy diet; causing the first computing device to present, via the user interface, nutritional information associated with the first item and the second item; prompting, via the user interface presented by the first computing device, the particular registered dietitian to confirm that the medical nutrition therapy diet comprising the first item and the second item satisfies the first patient's updated dietary restrictions including requirements associated with the first diet type; receiving, from the first computing device, an indication that input was received via the user interface confirming that the medical nutrition therapy diet satisfies the first patient's updated dietary restrictions; in response to receiving confirmation that the medical nutrition therapy diet satisfies the first patient's updated dietary restrictions, recording an indication that the particular registered dietitian approved the medical nutrition therapy diet as satisfying the first patient's updated dietary restrictions; and causing the medical nutrition therapy diet to be transmitted to a food service system to cause one or more meals to be prepared for the first patient at the facility based on the medical nutrition therapy diet.

In some embodiments, the system further comprises: a licensing database comprising information related to licensing requirements for registered dietitian in a plurality of jurisdictions indicating which of the plurality of jurisdictions require a license, and which of the plurality of jurisdictions grant reciprocity to dietitians licensed in particular other jurisdictions; wherein the at least one hardware processor that is further programmed to: submit a query to the licensing database for licensing requirements of a first jurisdiction; receive, from the licensing database, licensing requirements of the first jurisdiction; and determine that the particular registered dietitian is legally permitted to practice in the first jurisdiction based on the licensing requirements of the first jurisdiction and licensing information associated with the particular registered dietitian.

In some embodiments, the system further comprises: a privileges database comprising information identifying facilities for which each of a plurality of registered dietitians has received privileges to practice in that facility; wherein the at least one hardware processor that is further programmed to: submit a query to the privileges database for privileges requirements; and receive, from the privileges database, privilege information associated with the particular registered dietitian; determine that the particular registered dietitian has been granted privileges to practice at the facility based on the privilege information associated with the particular registered dietitian.

In some embodiments, the system further comprises: a food item nutrition database comprising information identifying, for each of a plurality of food items, a detailed list of ingredients, a plant where the food item was manufactured, and a production line where the food item was manufactured to identify the possibility of preparation and potential cross-contamination of the food item with an unlisted ingredient; wherein the at least one hardware processor that is further programmed to: submit a query to the food item nutrition database for food item nutrition information of a first food item; receive, from the food item nutrition database, nutrition information of the first food item; and determine that first food item satisfies one or more dietary restrictions, texture restrictions, liquid restrictions, allergen restrictions, and cross-contamination restrictions associated with the first patient based on the nutrition information of the first food item.

In some embodiments, the system further comprises: a health record database comprising electronic health record data; wherein the at least one hardware processor that is further programmed to: submit a query to the health record database for health record data associated with the first patient; receive, from the health record database, the health record data associated with the first patient; determine, based on the health record data associated with the first patient, that the first patient requires a medical nutrition therapy diet; determine, based on the health record data associated with the first patient, if there is an active medical order restricting a medical nutrition therapy diet; and determine, based on the health record data associated with the first patient, if the first patient has a health condition that requires a medical nutrition therapy diet.

BRIEF DESCRIPTION OF THE DRAWINGS

Various objects, features, and advantages of the disclosed subject matter can be more fully appreciated with reference to the following detailed description of the disclosed subject matter when considered in connection with the following drawings, in which like reference numerals identify like elements.

FIG. 4 shows an example of a portion of a diet spreadsheet for a facility for two meals with contingencies covering a variety of diet types.

FIG. 18 shows an example of a portion of a user interface for presenting patients needing attention in accordance with some embodiments of the disclosed subject matter.

FIG. 20 shows an example of a portion of a user interface for a summary of patient statuses across facilities in accordance with some embodiment of the disclosed subject matter.

DETAILED DESCRIPTION

In accordance with various embodiments, mechanisms (which can, for example, include systems, methods, and media) for automated dietary management in healthcare facilities are provided.

Figure 1:
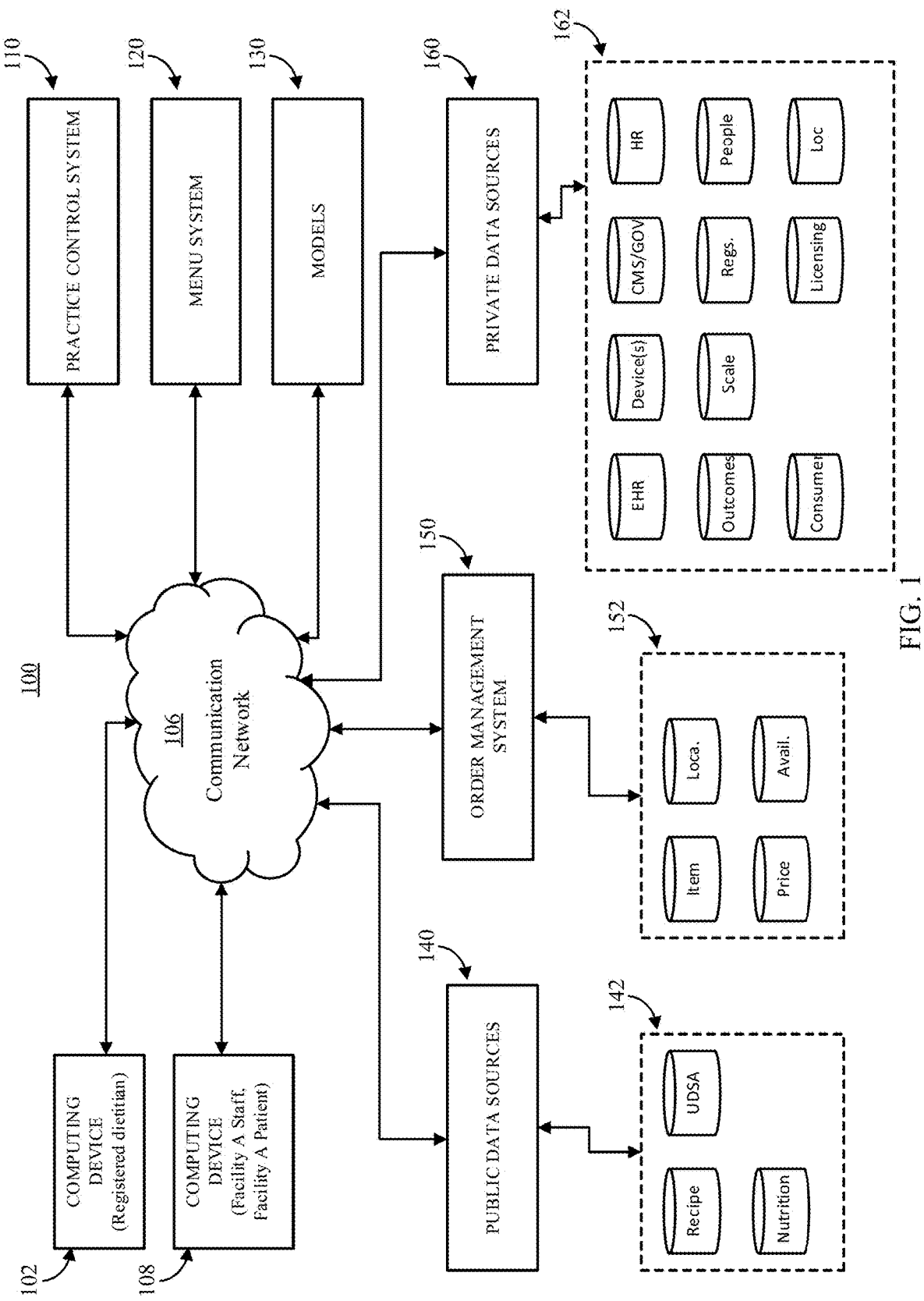
FIG. 1 shows an example of a system for facilitating practice by registered dietitians in remotely located healthcare facilities in accordance with some embodiments of the disclosed subject matter.

FIG. 1 shows an example 100 of a system for facilitating practice by registered dietitians in remotely located healthcare facilities in accordance with some embodiments of the disclosed subject matter. In some embodiments, system 100 can include a computing device 102 that can be utilized (e.g., by a registered dietitian) to interact with various portions of system 100 via a communications network 106. For example, in some embodiments, system 100 can include a practice control system 110, a menu system 120, one or more public data sources 140, an order management system 150, and one or more private data sources 160.

In some embodiments, computing device 102 can be any suitable computing device or combination of computing devices. For example, compute device 102 can include physical computing devices associated with a user (e.g., a personal computer, a laptop computer, a server, a smartphone, a tablet computer, a wearable computer, and so on), and virtual computing devices provided through a compute service (e.g., via one or more virtual machines). In some embodiments, computing device 102 can be provided by an employer or an organization that retains the services of a user (e.g., a registered dietitian) of computing device 102 as an independent contractor. For example, computing device 102 can be a personal computer, a laptop computer, a tablet computer, a smartphone, a virtual machine, one or more containers, and the like. that is associated with a particular facility. Note that although generally described as facilitating practice by registered dietitians that are remotely located from a facility (e.g., a regulated healthcare facility, a non-regulated healthcare facility, or any other suitable type of facility), system 100 can also be used to facilitate practice by a registered dietitian that is located locally. For example, computing device 102 can be a mobile or non-mobile computing device that is located within the facility at least a portion of the time that it is being used in connection with system 100. Examples of facilities that may utilize a registered dietitian to develop menus include skilled nursing facilities, assisted living facilities, hospitals, nursing homes, and community living facilities (sometimes referred to as group homes), which may or may not be regulated by various levels of government. For example, skilled nursing facilities are typically regulated at least by CMS at the federal level, and by agencies associated with one or more levels of state or local government. As another example, group homes are typically regulated, if at all, at the state level with relatively little regulation at the federal level. Other facilities and/or organizations (which may or may not be associated with a particular facility) may utilize a registered dietitian to develop menus using mechanisms described herein. For example, a school, a school system, a sports team (e.g., an amateur or professional team, club, etc.), or other organizations that may wish to develop a menu or menus that satisfy particular nutritional needs of individuals in a group (note that such nutritional needs may or may not be specified in government regulations).

In some embodiments, computing device 102 can, via communication network 106, interact with practice control system 110, menu system 120, one or more models 130, one or more public data sources 140, an order management system 150, and one or more private data sources 160. In some embodiments, communication network 106 can be any suitable wired network, wireless network, any other suitable network, or any suitable combination thereof. Additionally, communication network 106 can be any suitable personal area network, local area network, wide area network, over-the-air broadcast network (e.g., for radio or television), cable network, satellite network, cellular telephone network, any other suitable type of network, or any suitable combination thereof. For example, communication network 106 can include a publicly accessible network of linked networks, in some cases operated by various distinct parties, such as the Internet. In some embodiments, communication network 106 can include a private or semi-private network, such as a corporate or university intranet. Additionally, in some embodiments, communication network 106 can include one or more wireless networks, such as a Global System for Mobile Communications (GSM) network, a Code Division Multiple Access (CDMA) network, a Long Term Evolution (LTE) network, fifth Generation (5G) network, any other suitable wireless network, or any suitable combination of wireless networks. Communication network 106 can use any suitable protocols and/or components for communicating via the Internet and/or any of the other aforementioned types of networks. For example, communication network 106 can use one or more protocols or combinations or protocols, such as Hypertext Transfer Protocol (HTTP), HTTPS, Message Queue Telemetry Transport (MQTT), Constrained Application Protocol (CoAP), and so on.

In some embodiments, computing device 102 can interact with interact with practice control system 110 to authenticate a user of computing device 102, prompt a user of computing device 102 to perform one or more practice activities assigned to the user, to facilitate interactions with one or more other systems (e.g., menu system 120, models 130, public data sources 140, order management system 150, private data sources 160, computing devices associated with one or more facilities and/or patients), to facilitate practice activities under the user's responsibility, and/or to perform any other suitable functions. Additionally or alternatively, computing device 102 can interact with interact with practice control system 110 to prompt a user of computing device 102 to perform one or more user roles (e.g., registered dietitian, food service director, facility medical staffs, system administrator, or any organization defined role). In some embodiments, user roles can specify system privileges granted to a user based on an organization's policies, the user's role in the organization, information security constraints, information security policies, state and/or federal licensing requirements, and/or any other suitable metadata that can be used to define user constraints in practice control system 110. In some embodiments, a user role can be assigned to a user by an appropriate organization authority. System privileges granted to the user can facilitate and/or restrict particular interactions with one or more other systems and/or data (e.g., menu system 120, models 130, public data sources 140, order management system 150, private data sources 160, computing devices associated with one or more facilities and/or patients), which can facilitate practice activities under the user's responsibility.

In some embodiments, computing device 102 can submit a request for information from practice control system 110 via a frontend. In some embodiments, the frontend of practice control system 110 can request credential information from computing device 102 prior to providing information. For example, the frontend can redirect computing device 102 to a user interface that prompts a user to enter or otherwise provide credential information. In some embodiments, the credential information can be any suitable credential information, such as a username, a password, a hardware-based security token, a software-based security token, a one-time code, a biometric-based security token, any other suitable credentials, or any suitable combination of credentials. Note that in some embodiments, a user interface presented by computing device 102 can be generated by practice control system 110 and/or computing device 102. For example, a user interface can be generated based on instructions (e.g., HTML code, JavaScript) provided to computing device 102 by a web server that implements at least a portion of the frontend. In such an example, the instructions can be used by an application being executed by computing device 102 (e.g., a general purpose application such as a web browser, or a special purpose application such as an application associated with practice control system 110 that implements a portion of the frontend) to present the user interface. As another example, a user interface can be generated based on instructions generated by an application installed on and/or being executed by computing device 102 (e.g., a specialized application such as an application associated with practice control system 110 that implements a portion of the frontend). In some embodiments, the user interface presented by computing device 102 can be populated using data provided by practice control system 110 and/or any other system (e.g., a database housed outside of practice control system 110, which can be a third party database that is maintained by an organization that is not associated with practice control system 110, e.g., that is accessible via public data sources 140, order management system 150, and/or private data sources 160). For example, in some embodiments, computing device 102 can access data about locations for which a user of computing device 102 is responsible from a location database maintained by an organization that owns and/or operates the locations.

In some embodiments, system 100 can include a computing device 108 associated with a facility for which a menu is being developed and/or which is associated with one or more patients for whom one or more individual diets (e.g., corresponding to a particular diet type, which may be part of a medical nutrition therapy diet) are being developed (e.g., by a user of computing device 102). For example, computing device 108 can be a personal computer, a laptop computer, a tablet computer, a smartphone, a terminal, a virtual machine, one or more containers, and the like, that is associated with a particular facility. For example, computing device 108 can be supplied by an organization that owns and/or operates the particular facility. In such an example, the organization can control which applications are installed on computing device 108, and/or can control which user or users are provided with credentials that facilitate use of computing device 108. In some embodiments, the organization can install or facilitate installation of one or more applications (e.g., mobile applications, or desktop applications) on computing device 108 that can be used to interact with practice control system 110, menu system 120, and/or any other appropriate system. Additionally or alternatively, in some embodiments, the organization can facilitate access to one or more application (e.g., web applications) by computing device 108 by providing credentials and/or a process for obtaining credentials to a user of computing device 108.

In some embodiments, computing device 108 can be a device that is owned by an employee, patient, or other user associated with the facility. In such an example, the organization can facilitate the owner of the device in installing an application (e.g., as a mobile application, or a desktop application) or accessing an application (e.g., a web application) that can be used to interact with one or more portions of system 100. As another example, the organization can provide the owner of computing device 108 with access to a virtual machine controlled by the organization and/or an entity associated with one or more portions of system 100 that is configured to interact with one or more portions of system 100. In such an example, the organization can provide credentials to a user of computing device 108 that can be used to access the virtual machine, which can be configured interact with system 100 with or without additional credentials.

In some embodiments, models 130 can include one or more trained machine learning models that can be used to assist other portions of the system. Note that although models 130 is shown as a separate system that is connected to computing devices 102 and 108, practice control system 110, and menu system 120 via communication network 106, this is merely an example of such models being provided as a service that can be called on to provide such recommendations or classifications. Additionally or alternatively, one or more models can be hosted within another system such as computing device 102, computing device 108, practice control system 110, or menu system 120.

In some embodiments, models 130 can include any suitable model or models (e.g., machine learning models, algorithm-based optimizer models) configured to perform any suitable tasks. For example, models 130 can include a machine learning model trained to automatically select recipes for inclusion on a menu based on predetermined criteria, a machine learning model that identifies medical nutrition therapy diet effectiveness, and/or a machine learning model that identifies treatment options likely to lead to better outcomes. In some embodiments, models 130 can use various types of information available from various sources to select recipe selections, determine diet effectiveness, identify appropriate treatments, and so on. For example, models 130 can use data (e.g., measurable physiological data) that is indicative of a patient's response to their diet. Such data can include changes in weight or mass (e.g., weight loss or weight gain over time), changes in a metric indicative of weight (e.g., changes in body mass index), changes in blood pressure (e.g., reduction in systolic blood pressure over time, increase in systolic blood pressure over time), changes in blood glucose levels (e.g., reduction in blood glucose levels over time, increase in blood glucose levels over time), changes in blood cholesterol levels (e.g., reduction in blood cholesterol levels, increases in blood cholesterol levels), and the like, or lack of a change in one or more physiological variables.

As another example, models 130 can use data (e.g., based on user input and/or feedback from one or more devices used to determine consumption habits of patients) that is indicative of a patient's explicit and/or revealed preferences for various food types and/or ingredients. Such data can be used, for example, to select recipes that a particular patient is likely to find more appealing, as a medical nutrition therapy diet is less effective if the patient is not consuming the recipes that are prepared as part of the diet. Examples of patient preference can include regional cuisine, cultural cuisine, and/or individual preference.

As yet another example, models 130 can use data (e.g., based on a set of explicit rules, based on reinforcement learning, and/or based on any other suitable mechanism) that is indicative of regulatory requirements and/or corporate policies. Examples can include the minimum and/or maximum frequency of the primary protein used in a menu, the number of starches required and/or allowed to be present in a given meal.

As still another example, models 130 can use data (e.g., based on data maintained by the facility, based on data maintained by a vendor(s) that supplies ingredients to the facility) that is indicative of ingredient availability at the facility, as recipes can only be prepared if the ingredients are available.

As a further example, models 130 can use data (e.g., based on data maintained by a vendor(s) that supplies ingredients to the facility) that is indicative of ingredients that can be made available at the facility via the organization's food supply chain for recipes, which can be used by the trained machine learning models to determine if a recipe can be selected for a diet or menu.

As another further example, models 130 can use data (e.g., based on data maintained by a vendor(s) that supplies ingredients to the facility) that is indicative of ingredient cost that can be used to determine a cost associated with a recipe, which can be used as a constraint by models 130 to help the facility and/or organization control costs while ensuring that patients are provided with a selection of recipes that is appropriate to the patients' needs and satisfies applicable regulatory requirements.

As another further example, models 130 can use data (e.g., based on data maintained by the facility and/or by a vendor(s) that supplies ingredients to the facility) that is indicative of ingredient usage across recipes, as more frequently used ingredients tend to be preferred over less frequently used ingredients.

In some embodiments, in addition to, or in lieu of, trained machine learning models, models 130 can include one or more algorithm-based optimizer models (and/or any other suitable models) configured to perform various functions (e.g., function described above in connection with trained machine learning models). Such an algorithm-based optimizer model can be implemented using any suitable technique or combination of techniques, such as linear regression, cluster analysis, any other suitable statistical modeling technique, or any suitable combination of statistical modeling techniques, to generate recommendations based on relationships in data used to develop such as model. For example, an algorithm-based optimizer model can be configured to automatically select recipes for inclusion on a menu based on predetermined criteria. As another example, an algorithm-based optimizer model can be configured to identify medical nutrition therapy diet effectiveness. As yet another example, an algorithm-based optimizer model can be configured to identify treatment options likely to lead to better outcomes. In some embodiments, an algorithm-based optimizer model can be configured to use various types of information available from various sources to select recipe selections, determine diet effectiveness, identify appropriate treatments, and so on. For example, an algorithm-based optimizer model can use data (e.g., measurable physiological data) that is indicative of a patient's response to their diet. Such data can include changes in weight (e.g., weight loss or weight gain over time), changes in blood pressure (e.g., reduction in systolic blood pressure over time, increase in systolic blood pressure over time), changes in blood glucose levels (e.g., reduction in blood glucose levels over time, increase in blood glucose levels over time), changes in blood cholesterol levels (e.g., reduction in blood cholesterol levels, increases in blood cholesterol levels), and the like, or lack of a change in one or more physiological variables.

In some embodiments, public data sources 140 can include various public databases 142, such as one or more recipe databases, one or more nutrition databases, and/or one or more databases made available by the United States Department of Agriculture (USDA). In some embodiments, public data sources 140 can be used to refer to sources that are simply available publicly (e.g., for free), and which may require credentials to access. Additionally or alternatively, in some embodiments, public data sources 140 can be a system configured to provide access to one or more public data sources and/or configured to mirror one or more public data sources. For example, in some embodiments, public data sources 140 can be a system that is used to implement one or more application program interfaces (APIs) that are configured to provide access between practice control system 110, menu system 120, and/or models 130 and public databases 142.

In some embodiments, order management system 150 can be used by an organization and/or facility to harmonize procurement activities from one or more distributors. For example, order management system 150 can be used to generate an order guide that can be associated with a particular facility or facilities and used to populate a user interface of an order procurement system. In some embodiments, order management system 150 can provide access to one or more order management databases 152, such as an item database, a pricing database, a locations database, an availability database. In some embodiments, item and pricing databases can include information about items that can be ordered by various facilities and/or information about a price associated with the items. In some embodiments, item and pricing databases can be maintained as part of order management system 150 and/or can be populated using information from order management system 150.

In some embodiments, private data sources 160 can include various private databases and/or other sources of private data 162, such as electronic health records, information related to patient outcomes, information from one or more devices (e.g., personal health devices, connected scales), business records (e.g., a database of evaluation information (e.g., Tags) generated by the Centers for Medicare and Medicaid Services (CMS), evaluation information generated by one or more other regulators (e.g., local or state regulators)), a curated database of pertinent regulations, a database of licensing information, human resources records for one or more healthcare providers, a database of information about patients that is not included elsewhere (e.g., not included in an electronic health record), and/or any other suitable information.

Note that, in some embodiments, information stored in public databases 142, order management databases 152, and/or private databases 162 can be stored in a distributed database and/or distributed record that is maintained across various computing devices in a network of computing devices. For example, in some embodiments, such data can be stored using blockchain techniques to store and update data in an encrypted and distributed record. As another example, such data can be stored using a secured (e.g., password protected) and encrypted database (e.g., implemented using relational and/or non-relational data stores) to securely store and update data. In a more particular example, structured query language (SQL) techniques can be used to implement a relational database. As another more particular example, NoSQL techniques can be used to implement a non-relational database.

Figure 2:
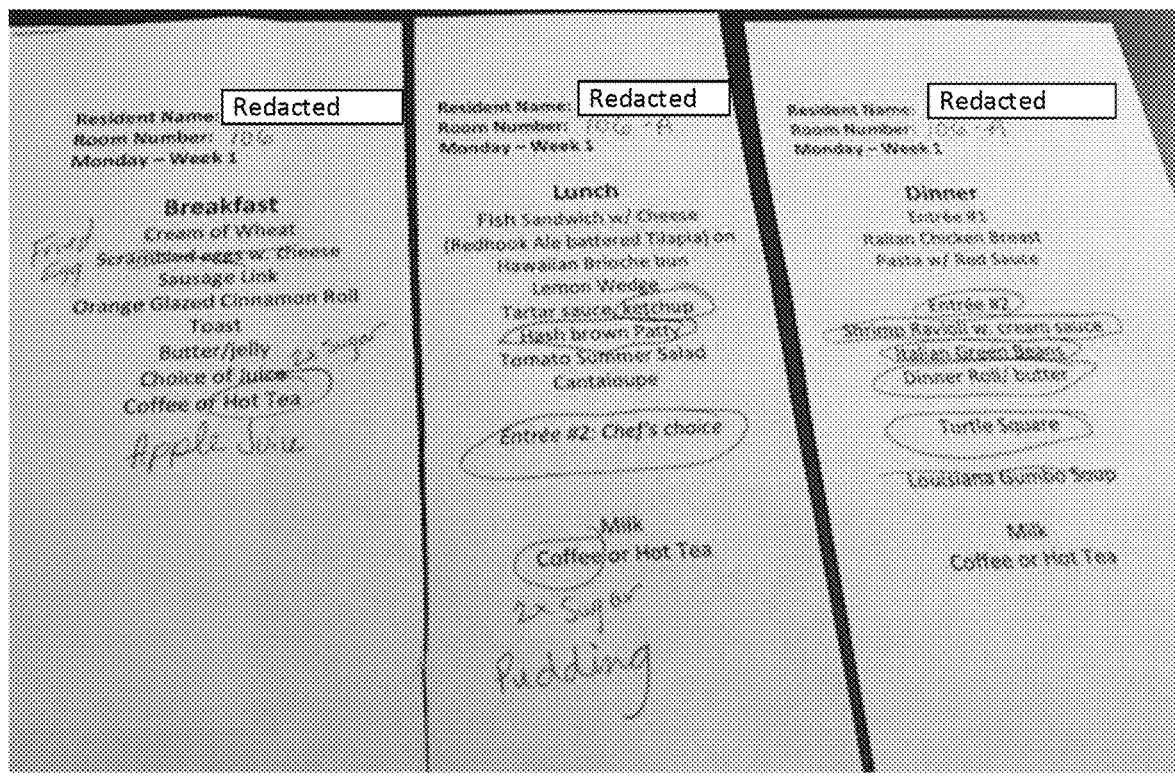
FIG. 2 shows an example of a paper-based meal selection system.
Figure 3:
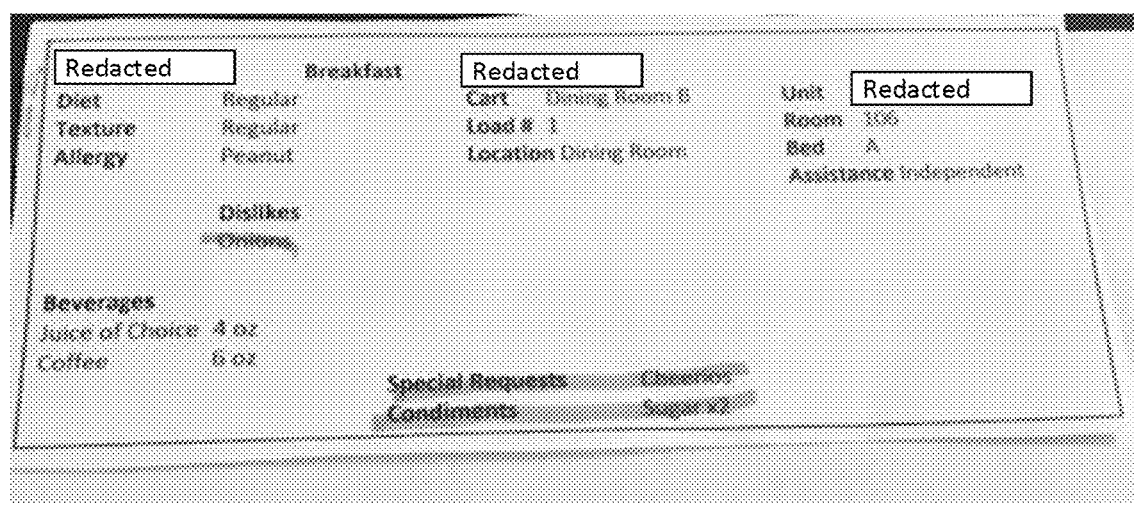
FIG. 3 shows an example of a paper tray card used to prepare and serve a meal in a paper-based meal selection system.

FIG. 2 shows an example of a paper-based meal selection system, and FIG. 3 shows an example of a paper tray card used to prepare and serve a meal in a paper-based meal selection system. As shown in FIG. 2, many facilities use paper systems to solicit input from residents regarding the residents' meal choices. The meal choices are often used to populate a tray card that will be used when assembling the meals for each resident. The information in the tray card can help insure that special requests are honored, and that the meal being served complies with any special dietary needs or restrictions of the resident, such as a diet type (e.g., corresponding to a particular type of therapeutic diet), texture restrictions, or allergies.

FIG. 4 shows an example of a portion of a diet spreadsheet for a facility for two meals with contingencies covering a variety of diet types. The portion of the diet spreadsheet shown in FIG. 4 represents two meals on a single day, and illustrates the need to plan for contingencies for multiple different types of diets to which residents of healthcare facilities may be required to adhere. In many jurisdictions, certain types of healthcare facilities are regulated by one or more government entities. In such regulated facilities, the regular menu must comply with certain nutritional and calorie requirements, as well as being palatable to the residents of the facility. In addition to these constraints, the facility must source the ingredients for the menu from particular suppliers within a particular budget. The person or persons responsible for developing the menu must consider all of these constraints when developing just the regular diet for each day, and in many jurisdictions, a registered dietitian may be required to certify that the menu complies with applicable regulations. Complicating these considerations further, alternatives must be developed for each different type of diet that must be served and/or is likely to be served at the facility. For example, as shown in FIG. 4, substitutions must be found for oatmeal to comply with the pureed diet, finger food diet, and fortified diet, and another set of substitutions must be found for apple pie, and so on.

Figure 5:
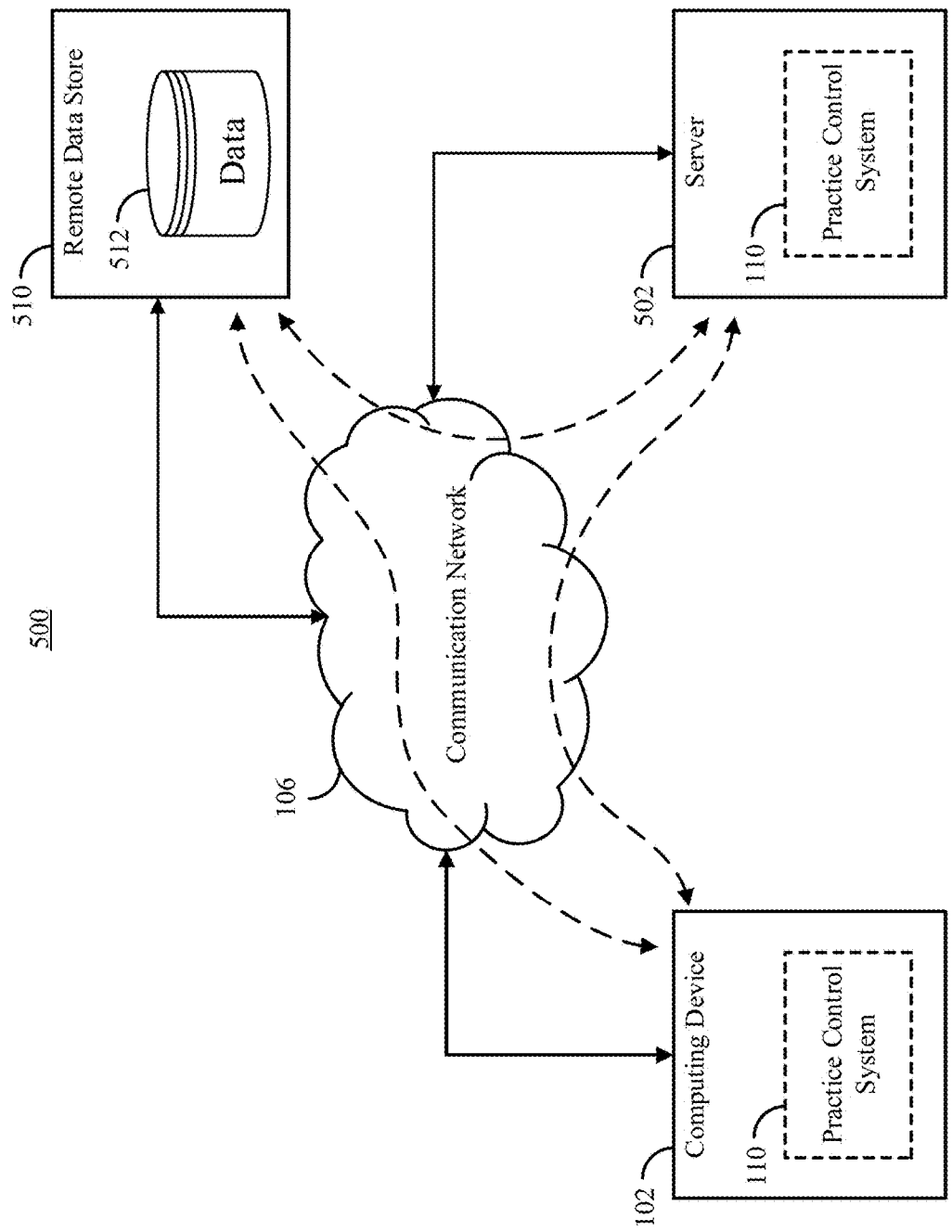
FIG. 5 shows an example of components of a system for registered dietitian practice management in healthcare facilities in accordance with some embodiments of the disclosed subject matter.

FIG. 5 shows an example 500 of components of a system for registered dietitian practice management in healthcare facilities in accordance with some embodiments of the disclosed subject matter. As shown in FIG. 5, a server (or other processing unit) 502 can execute one or more applications to provide access to one or more portions of practice control system 110. In some embodiments, practice control system 110 can facilitate one or more critical functions that must be performed as part of a registered dietitian's duties, such as patient consults, diet development, menu updates, menu validation, surveys. Additionally, in some embodiments, practice control system 110 can facilitate the remote performance of such functions through the use of technology to connect registered dietitians with patients (e.g., to perform consultations) and/or to ensure compliance with applicable regulations in which the registered dietitian is not physically located.

In some embodiments, server 502, and/or practice control system 110 can receive requests for information, queries, user input, and/or any other suitable data, over communication network 106. In some embodiments, such information can be received from any suitable computing device, such as computing device 102 and/or computing device 108. For example, computing device 102 can receive user input through an application being executed by computing device 102, such as through an input device (e.g., a keyboard, mouse, microphone, touchscreen, and the like). In such an example, computing device 102 can communicate information over communication network 106 to server 502 (or another server that can provide the information to server 202). As shown in FIG. 5, practice control system 110 can be implemented using computing device 102 and/or server 502. For example, server 502 can be used to implement at least a portion of a back-end of practice control system 110 and computing device 102 can be used to implement at least a portion of a front-end of practice control system 110, such as a user interface.

In some embodiments, server 502 can communicate with one or more computing devices, such as a remote data store 510 that hosts one or more databases 512 (e.g., electronic health records, outcomes, and so on), to collect information regarding a current diet order for one or more patients, past diet orders for one or more patients, other health information associated with the one or more patients, and so on. Note that, in some embodiments, database 512 can be implemented as a distributed database and/or distributed record that is maintained across various computing devices in a network of computing devices (i.e., remote data store 510 can include multiple computing devices in a network of computing devices). For example, in some embodiments, database 512 can use blockchain techniques to store and update data in an encrypted and distributed record. As another example, database 512 can be implemented as a secured and encrypted database (e.g., implemented using relational and/or non-relational data stores) to securely store and update data.

In some embodiments, server 502 can communicate with one or more remote data stores 510 to collect information that can be used to perform critical activities associated with a registered dietitians practice, such as performing patient consults, generating a menu for a particular facility, verify that a menu is in compliance with one or more constraints (e.g., imposed by the registered dietitian, a local government, a state government, the federal government), and so on.

In some embodiments, communications links shown in FIG. 5 can each be any suitable communications link or combination of communications links, such as wired links, fiber optic links, Wi-Fi links, Bluetooth links, cellular links, and the like. In some embodiments, server 502, computing device 102, and/or computing device 108 can be any suitable computing device or combination of devices, such as a desktop computer, a laptop computer, a smartphone, a tablet computer, a wearable computer, a server computer, and the like. Additionally, in some embodiments, functionality associated with server 502, computing device 102, and/or computing device 108 can be provided via one or more virtual machines being executed by a physical computing device (e.g., locally and/or remotely), one or more containers (e.g., executed by a virtual machine or by a physical machine directly, locally and/or remotely), and the like. In some such embodiments, server 502, computing device 102, and/or computing device 108 can act as a terminal that is used to access remote compute resources (e.g., remote virtual machines, remote containers, and the like).

In some embodiments, communications transmitted over communication network 106 and/or communication links shown in FIG. 5 can be secured using any suitable technique or combination of techniques. For example, in some embodiments, communications transmitted to and/or from server 502, computing device 502, and/or data store 510 can be encrypted using any suitable technique or combination of techniques. For example, communication between two or more computing devices associated with communication network 106 (e.g., Server 202, computing device 102, data store 510, Domain Name System (DNS) servers, one or more intermediate nodes that serve as links between two or more other devices, such as switches, bridges, routers, modems, wireless access points, and the like) computing devices can be carried out based on Hypertext Transfer Protocol Secure (HTTPS). As another example, communications can be carried out based on Transport Layer Security (TLS) protocols and/or Secure Sockets Layer (SSL) protocols. As yet another example, communications can be carried out based on Internet Protocol Security (IPsec) protocols. As still another example, a virtual private network (VPN) connection can be established between one or more computing devices associated with computing network 106. In some embodiments, one or more techniques can be used to limit access to communication network 106 and/or a portion of communication network 106. For example, computing devices attempting to connect to the network and/or transmit communications using the network can be required to provide credentials (e.g., a username, a password, a hardware-based security token, a software-based security token, a one-time code, any other suitable credentials, or any suitable combination of credentials).

In some embodiments, one or more security techniques can be applied to any suitable portion of a communication network that interacts with computing devices. For example, security techniques can be used to implement a secure Wi-Fi network (which can include one or more wireless routers, one or more switches, and the like), a secure peer-to-peer network (e.g., a Bluetooth network), a secure cellular network (e.g., a 3G network, a 4G network, a 5G network, and the like, complying with any suitable standard(s), such as CDMA, GSM, LTE, LTE Advanced, WiMAX, 5G NR, and the like), and the like.

Figure 6:
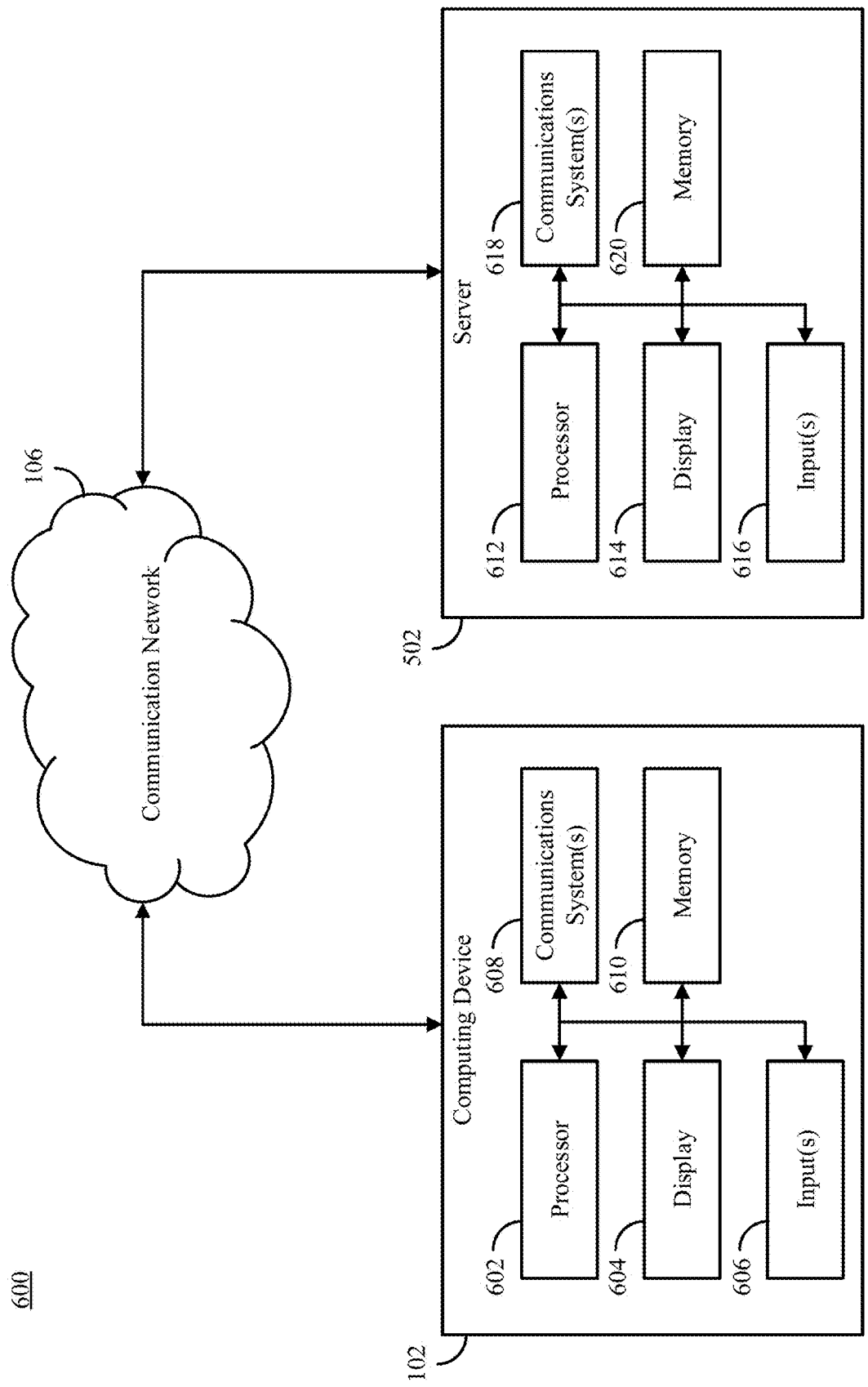
FIG. 6 shows an example of hardware that can be used to implement a server and a computing device in accordance with some embodiments of the disclosed subject matter.

FIG. 6 shows an example 600 of hardware that can be used to implement server 502 and computing device 102 in accordance with some embodiments of the disclosed subject matter. As shown in FIG. 6, in some embodiments, computing device 102 can include a processor 602, a display 604, one or more inputs 606, one or more communication systems 608, and/or memory 610. In some embodiments, processor 602 can be any suitable hardware processor or combination of processors, such as a central processing unit (CPU), a graphics processing unit (GPU), and the like. In some embodiments, display 604 can include any suitable display devices, such as a computer monitor, a touchscreen, a television, and the like. In some embodiments, inputs 606 can include any suitable input devices and/or sensors that can be used to receive user input, such as a keyboard, a mouse, a touchscreen, a microphone, a camera, and the like.

In some embodiments, communications systems 608 can include any suitable hardware, firmware, and/or software for communicating information over communication network 106 and/or any other suitable communication networks. For example, communications systems 608 can include one or more transceivers, one or more communication chips and/or chip sets, and the like. In a more particular example, communications systems 608 can include hardware, firmware and/or software that can be used to establish a Wi-Fi connection, a Bluetooth connection, a cellular connection, an Ethernet connection, and the like.

In some embodiments, memory 610 can include any suitable storage device or devices that can be used to store instructions, values, and the like, that can be used, for example, by processor 602 to present content using display 604, to communicate with server 202 via communications system(s) 608, and the like. Memory 610 can include any suitable volatile memory, non-volatile memory, storage, or any suitable combination thereof. For example, memory 610 can include RAM, ROM, EEPROM, one or more flash drives, one or more hard disks, one or more solid state drives, one or more optical drives, and the like. In some embodiments, memory 610 can have encoded thereon a computer program for controlling operation of computing device 102. In such embodiments, processor 602 can execute at least a portion of the computer program to present content (e.g., user interfaces, tables, graphics, and the like), receive content from server 502, transmit information to server 502, and the like.

In some embodiments, server 502 can be implemented using one or more servers 502 (e.g., functions described as being performed by server 502 can be performed by multiple servers acting in concert) that can include a processor 612, a display 614, one or more inputs 616, one or more communications systems 618, and/or memory 620. In some embodiments, processor 612 can be any suitable hardware processor or combination of processors, such as a CPU, a GPU, and the like. In some embodiments, display 614 can include any suitable display devices, such as a computer monitor, a touchscreen, a television, and the like. In some embodiments, inputs 616 can include any suitable input devices and/or sensors that can be used to receive user input, such as a keyboard, a mouse, a touchscreen, a microphone, and the like. In some embodiments, server 502 can be a mobile device.

In some embodiments, communications systems 618 can include any suitable hardware, firmware, and/or software for communicating information over communication network 106 and/or any other suitable communication networks. For example, communications systems 618 can include one or more transceivers, one or more communication chips and/or chip sets, and the like. In a more particular example, communications systems 618 can include hardware, firmware and/or software that can be used to establish a Wi-Fi connection, a Bluetooth connection, a cellular connection, an Ethernet connection, and the like.

In some embodiments, memory 620 can include any suitable storage device or devices that can be used to store instructions, values, and the like, that can be used, for example, by processor 612 to present content using display 614, to communicate with one or more computing devices 102, and the like. Memory 620 can include any suitable volatile memory, non-volatile memory, storage, or any suitable combination thereof. For example, memory 620 can include RAM, ROM, EEPROM, one or more flash drives, one or more hard disks, one or more solid state drives, one or more optical drives, and the like. In some embodiments, memory 620 can have encoded thereon a server program for controlling operation of server 502. In such embodiments, processor 612 can execute at least a portion of the server program to transmit information and/or content (e.g., results of a database query, a portion of a user interface, textual information, graphics, and the like) to one or more computing 102, receive information and/or content from one or more computing devices 102, receive instructions from one or more devices (e.g., a personal computer, a laptop computer, a tablet computer, a smartphone, and the like), and the like. Note that although not shown in FIGS. 5 and 6, computing device 108 can be implemented using technique and components described above in connection with computing device 102.

Figure 7:
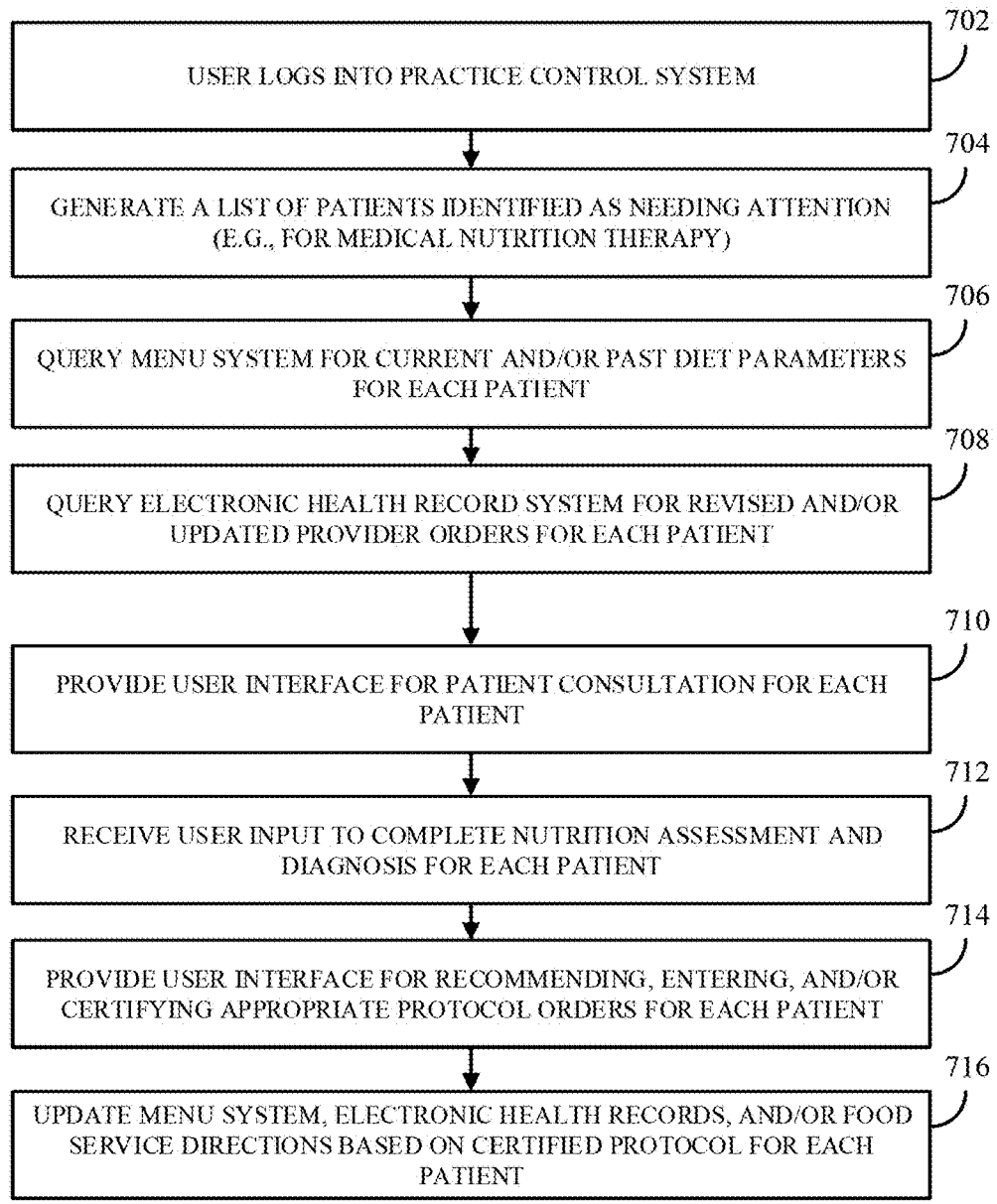
FIG. 7 shows an example of a process for facilitating practice management for registered dietitians in healthcare facilities in accordance with some embodiments of the disclosed subject matter.

FIG. 7 shows an example 700 of a process for facilitating practice management for registered dietitians in healthcare facilities in accordance with some embodiments of the disclosed subject matter. As shown in FIG. 7, at 702, a user can log into an application associated with a practice control system, and the user's credentials can be verified. For example, a user can attempt to log in to practice control system 110 via an application executed by computing device 102, and the user's credentials can be verified using any suitable technique or combination of techniques. For example, the user can be prompted to provide a username, a password, a hardware-based security token, a software-based security token, a one-time code, a biometric-based security token, any other suitable credentials, or any suitable combination of credentials. In some embodiments, at 702, process 700 can determine an identity of the user that is logging into the system based on the supplied credentials.

At 704, process 700 can generate a list of patients identified as needing attention, such as needing a patient consultation, or needing medical nutrition therapy. In some embodiments, at 704, process 700 can identify, from a list of patients associated with a particular facility and/or organization, a sub-group of patients that have been assigned to the user that logged in at 702. For example, in some embodiments, a particular registered dietitian can be associated with a particular facility and/or organization on a particular day based on the registered dietitian being licensed to practice in the jurisdiction in which the facility is located and/or based on the registered dietitian having capacity to perform tasks associated with the facility and/or organization.

In some embodiments, a patient can be identified as being in need of attention for a variety of reasons. For example, various actions may automatically or manually trigger the need to perform an assessment or reassessment of a patient within a set period of time. Particular examples can include a nutrition referral from a provider (e.g., a doctor, a nurse, or the like), the length of stay at a particular facility can trigger the need for a reassessment (e.g., based on a local, state, or federal regulation), a change in weight, a scheduled follow up, a pharmacy check, an admission, or a discharge. Such examples can trigger the need to perform a patient consultation to determine whether a change in diet is called for, whether supplemental intervention is called for, and/or whether additional or different education of the patient and/or providers is called for.

At 706, process 700 can query a menu system, menu database, and/or menu records, to determine current and/or past diet parameters for each patient. In some embodiments, patient diet information can be stored using any suitable technique or combination of techniques. For example, in some embodiments, patient diet parameters can be stored in a patient's electronic health records. As another example, patient diet parameters can be stored in memory and/or a data store of a menu system that serves a facility associated with the patient. As yet another example, patient diet parameters can be stored in a distributed database and/or distributed record that is maintained across various computing devices in a network of computing devices. For example, in some embodiments, patient diet parameters can be stored using blockchain techniques to store and update patient diet parameters in an encrypted and distributed record. As another example, patient diet parameters can be stored using a secured and encrypted database (e.g., implemented using relational and/or non-relational data stores) to securely store and update patient diet parameters.

In some embodiments, at 706, process 700 can receive and decrypt current and/or past diet parameters associated with each patient. In such embodiments, the amount of past diet parameters that are retrieved for each patient can vary, and can be adjusted based on the needs of the user and/or the anticipated needs of the user.

At 708, process 700 can query an electronic health record system for revised and/or updated provider orders for each patient. For example, process 700 can query an electronic health record system for any pertinent orders related to diet that have been provided by a medical provider such as a doctor, nurse practitioner, physician assistant, dentist, or the like.

In some embodiments, at 708, process 700 can receive information from the electronic health record system related to diet orders. In some embodiments, process 700 can compare a most recent order related to diet received from the electronic health record system to a most recent order stored in a practice control system for that patient to determine whether any changes have been made by a medical practitioner.

At 710, process 700 can generate and/or provide a user interface for patient consultation with each patient needing attention, and can populate the user interface using information received in response to the queries submitted at 706 and/or 708. In some embodiments, at least a portion of the user interface can be generated by practice control system 110, such as content used to populate at least a portion of the user interface, and another portion of the user interface can be generated by computing device 102 using an application being executed by the computing device.

At 712, process 700 can receive user input to complete a nutrition assessment and/or diagnosis for each patient identified at 704 as needing attention and being assigned to the user that logged in at 702. In some embodiments, process 700 can determine whether the nutrition assessment and/or diagnosis is complete by determining whether required fields have been completed.

At 714, process 700 can provide a user interface for recommending, entering, and/or certifying appropriate protocol orders for each patient identified at 704. In some embodiments, process 700 can generate recommendations of protocols for each patient based on the information received from the electronic health records system and/or the information input at 712, and can prepopulate the user interface provided at 714 with such recommendations. Additionally, in some embodiments, the user interface can be configured to permit the user to enter a new and/or adjusted protocol for each patient. In some embodiments, process 700 can prompt the user to certify a protocol for each patient that was identified at 704 as part of a required workflow for the user. In some embodiments, the prepopulated user interface can include information that can inform a user about prior diet orders and medically recommended protocols as a starting point to create a diet order for the patient. By providing a prepopulated baseline (e.g., populated using models 130) from which the user can construct the diet order, routine work can be omitted from the user's workflow, optimizing the time the user spends to craft a diet order that is appropriate for the patient. As described above in connection with models 130, process 700 can receive output from one or more models (e.g., machine learning models, algorithm-based optimizer models) that used various input data to identify information used to populate the user interface. Examples of such data can include data indicative of a patient's response to their diet, data indicative of a patient's explicit and/or revealed preferences for various food types, data indicative of regulatory requirements and/or corporate policies, data indicative of ingredient availability at the facility, data indicative of ingredients that can be made available at the facility via the organization's food supply chain, data that is indicative of ingredient cost that can be used to determine a cost associated with recipes, data that is indicative of ingredient usage across recipes, and/or any other suitable data.

In some embodiments, the prepopulated user interface presented at 714 can include recommendations received from one or more models (e.g., trained machine learning models, algorithm-based optimizer models). For example, the prepopulated user interface can be used to recommend changes to a patient's diet (e.g., to a medical nutrition therapy diet) based on changes (e.g., negative or positive changes) observed in physiological data associated with the patient, or a lack of changes in response to the patient's current diet. As another example, the prepopulated user interface can be used to recommend changes to ingredients in recipes based on changes in the ingredient availability at the facility. As yet another example, the prepopulated user interface can be used to suggest a new recipe(s) based on new and/or updated patient preference data. As still another example, the prepopulated user interface can be used to suggest a new recipe(s) based on aggregated patient preference data. FIG. 18 shows an example of a user interface that can be presented with pre-populated recommendations for particular patients based on output from a model.

At 716, process 700 can update a menu system, the patients' electronic health records, and/or food service directions associated with each patient to reflect the protocol certified for each patient at 714 to ensure that the patient begins receiving an appropriate diet.

In some embodiments, process 700 can update the menu system (e.g., menu system 120) with an indication that a particular patient's diet parameters have changed, which can lead to an automatic update in the menu system and/or can lead to the user being prompted to make changes within the menu system.

Figure 8:
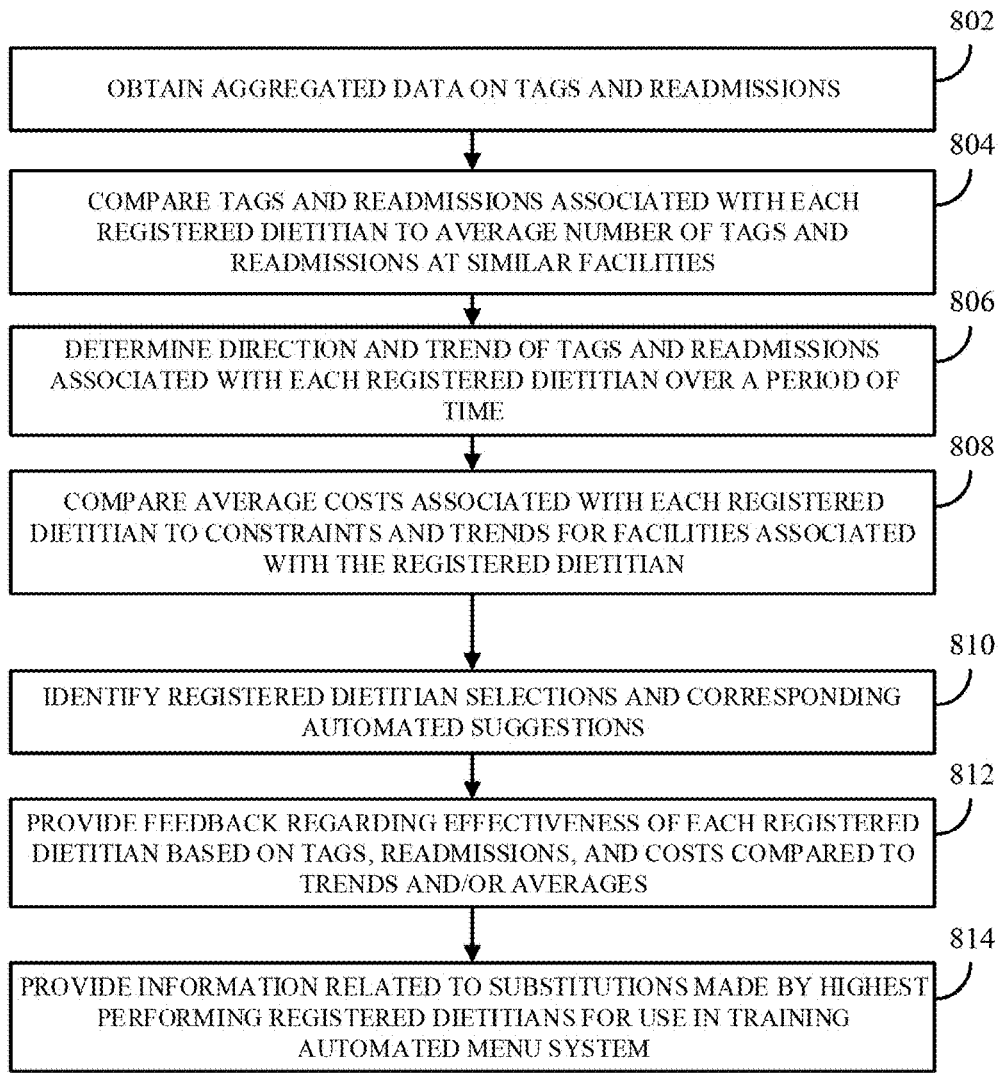
FIG. 8 shows an example of a process for generating feedback for improving a system for automated dietary management in healthcare facilities in accordance with some embodiments of the disclosed subject matter.

FIG. 8 shows an example 800 of a process for generating feedback for improving a system for automated dietary management in healthcare facilities in accordance with some embodiments of the disclosed subject matter. At 802, process 800 can obtain aggregated data on tags related to diet and nutrition and readmissions for residents and/or patients at facilities for which registered dietitians have at least partial responsibility for developing menus. In some embodiments, the tags can be queried and/or filtered based on metadata associated with the tags. For example, the tags can be queried and/or filtered based on metadata identifying an organization, facility, registered dietitian, patient, menu, diet (e.g., one or more medical nutrition therapy diets developed by a registered dietitian), diet type, and/or any other suitable person, place, or thing, associated with the tag.

In the description of FIG. 8, tags refer to F-Tags for Skilled Nursing Facilities and A-Tags for acute-care hospitals that indicate that a particular facility was found to be deficient under a particular federal regulation. Accordingly, the number of tags that are assessed to a facility and the tag numbers can be an indicator of performance for the facility and for staff associated with the facility (e.g., a registered dietitian that has a role in developing the menus for the facility).

At 804, process 800 can compare tabs and/or readmissions associated with each registered dietitian to an average number of tags and readmissions at similar facilities. Additionally or alternatively, in some embodiments, readmissions can be compared to similar facilities, rather than amongst registered dietitians as it can be difficult to determine from readmission statistics whether a particular readmission was related to diet.

At 806, process 800 can determine a direction and trend of tags and readmissions associated with each registered dietitian over a period of time. For example, in some embodiments, process 800 can determine whether the number of tags increased or decreased over the past year. As another example, in some embodiments, process 800 can determine whether the number of readmissions increased or decreased over the past year.

At 808, process 800 can compare average costs associated with each registered dietitian to constants and trends for facilities associated with the registered dietitian. For example, the predicted costs (e.g., the cost calculated by a menu generation system and/or menu verification system described below in connection with FIGS. 13 to 16) of menus prepared by the registered dietitian can be compared to the budgeted costs for the facility. As another example, the trend in food spending (e.g., per capita) or the facilities can be identified to determine whether it has been increasing or decreasing.

At 810, process 800 can identify times when each registered dietitian made a substitution or other change to a menu, and can determine how the change affected the compliance of the menu to the constraints. For example, whether the change increased or decreased the cost, whether the change brought the menu into compliance with one or more regulatory requirements, or caused the menu to be non-compliance with one or more regulatory requirements.

At 812, process 800 can provide feedback regarding the effectiveness of each registered dietitian based on the tags, readmissions, and costs compared to trends and/or averages among the registered dietitians in general.

At 814, process 800 can identify the most effective registered dietitians, and can provide information related to the substitutions and/or other changes that those most effective registered dietitians made for use in further training an automated menu selection system (e.g., a machine learning model used by practice control system 110, a machine learning model used by a menu generation system, an algorithm-based optimizer model used by practice control system 110, an algorithm-based optimizer model used by a menu generation system).

Figure 9:
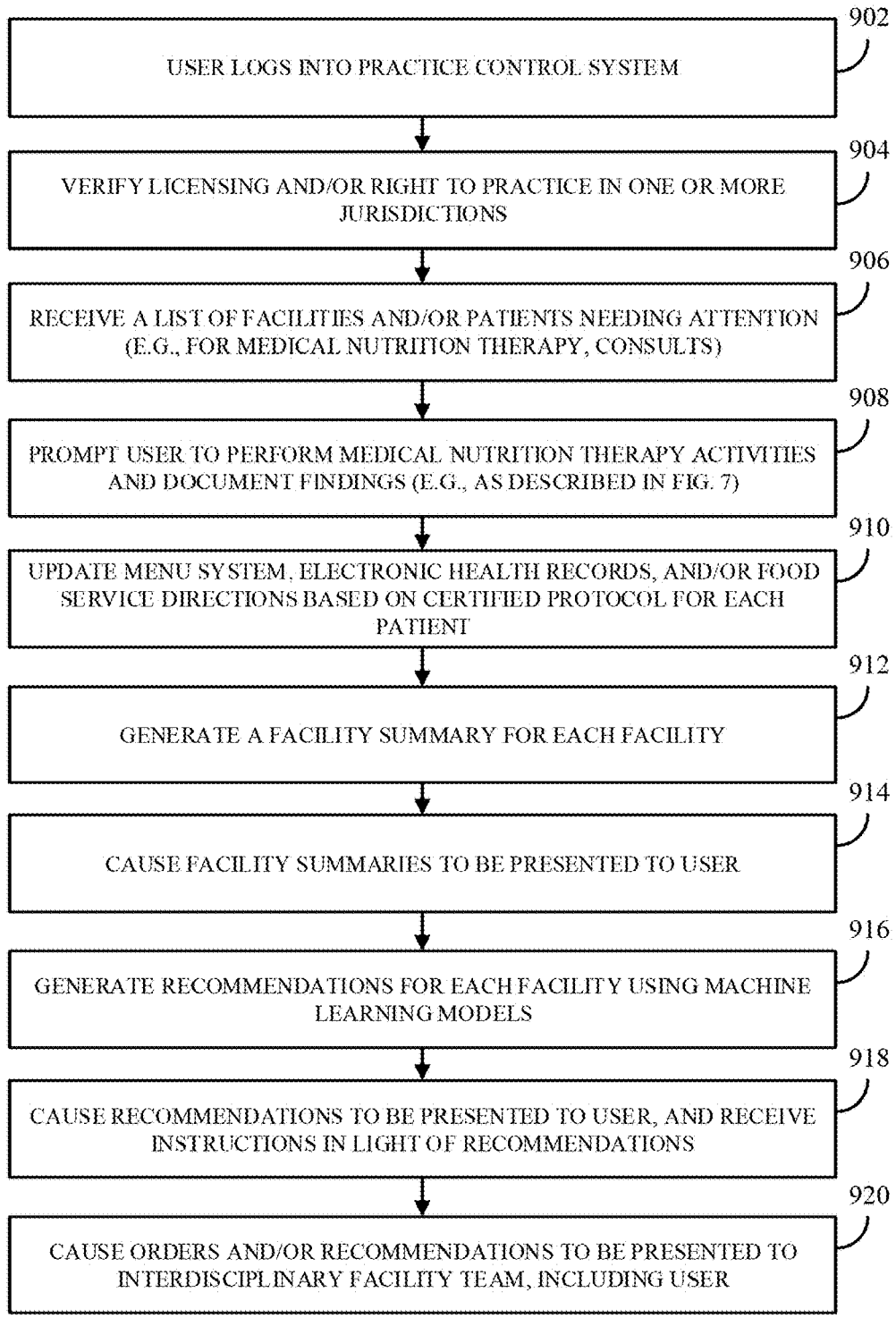
FIG. 9 shows an example of a process for facilitating compliance with dietary regulations in healthcare facilities in accordance with some embodiments of the disclosed subject matter.

FIG. 9 shows an example of a process for facilitating compliance with dietary regulations in healthcare facilities in accordance with some embodiments of the disclosed subject matter. At 902, process 900 a user (e.g., a registered dietitian) can log into an application associated with a practice control system, and the user's credentials can be verified. For example, a user's credentials can be verified as described above in connection with 702 of FIG. 7.

At 904, process 900 can verify the user's licensing information and/or right to practice in one or more jurisdictions based on the user's physical location, jurisdictions in which the user is currently licensed, and the regulations in one or more jurisdictions in which the user could potentially practice based on need. For example, certain jurisdictions do not have any licensing or physical presence requirements, and thus a registered dietitian can always practice in such a jurisdiction. As another example, some jurisdictions have very strict licensing and physical presence requirements that limit practice to registered dietitians licensed in the jurisdiction that are also physically present in the jurisdiction.

In some embodiments, process 900 can verify the user's current license status (e.g., by querying one or more databases maintained by jurisdictions and/or third parties, or by checking an internal database based on self-reported licensure information), and can determine the user's current location based on location information sent from the computing device used to log in at 902 (e.g., based on GPS signals, based on cellular signals, and/or using any other technique or combination of techniques).

At 906, process 900 can receive a list of facilities and/or patients needing attention, and can cross-reference the list with the jurisdictions in which the user is licensed to practice. In some embodiments, process 900 can select any suitable subset of the facilities and/or patients to assign to the user that logged in at 902.

At 908, process 900 can prompt the user to perform medical nutrition therapy activities and to document the user's findings for the assigned facilities and/or patients. For example, medical nutrition therapy activities can involve performing patient assessments and/or consults, and selecting and/or certifying diet protocols for patients, as described above in connection with FIG. 7.

At 910, process 900 can update a menu system, the patients' electronic health records, and/or food service directions associated with each patient to reflect the protocol certified for each patient selected as part of process 700 described above in connection with FIG. 7.

At 912, process 900 can generate a facility summary for each facility. In some embodiments, the facility summary can include any suitable information. For example, the facility summary can include the diet types present at the facility, the meal option selections for the facility, products ordered for that facility to support a diet for a particular patient (e.g., not as part of the general menu at the facility). As another example, the facility summary can include information about changes over time at the facility (e.g., presented as a chart, as a table, or in any other suitable format).

Figure 19:
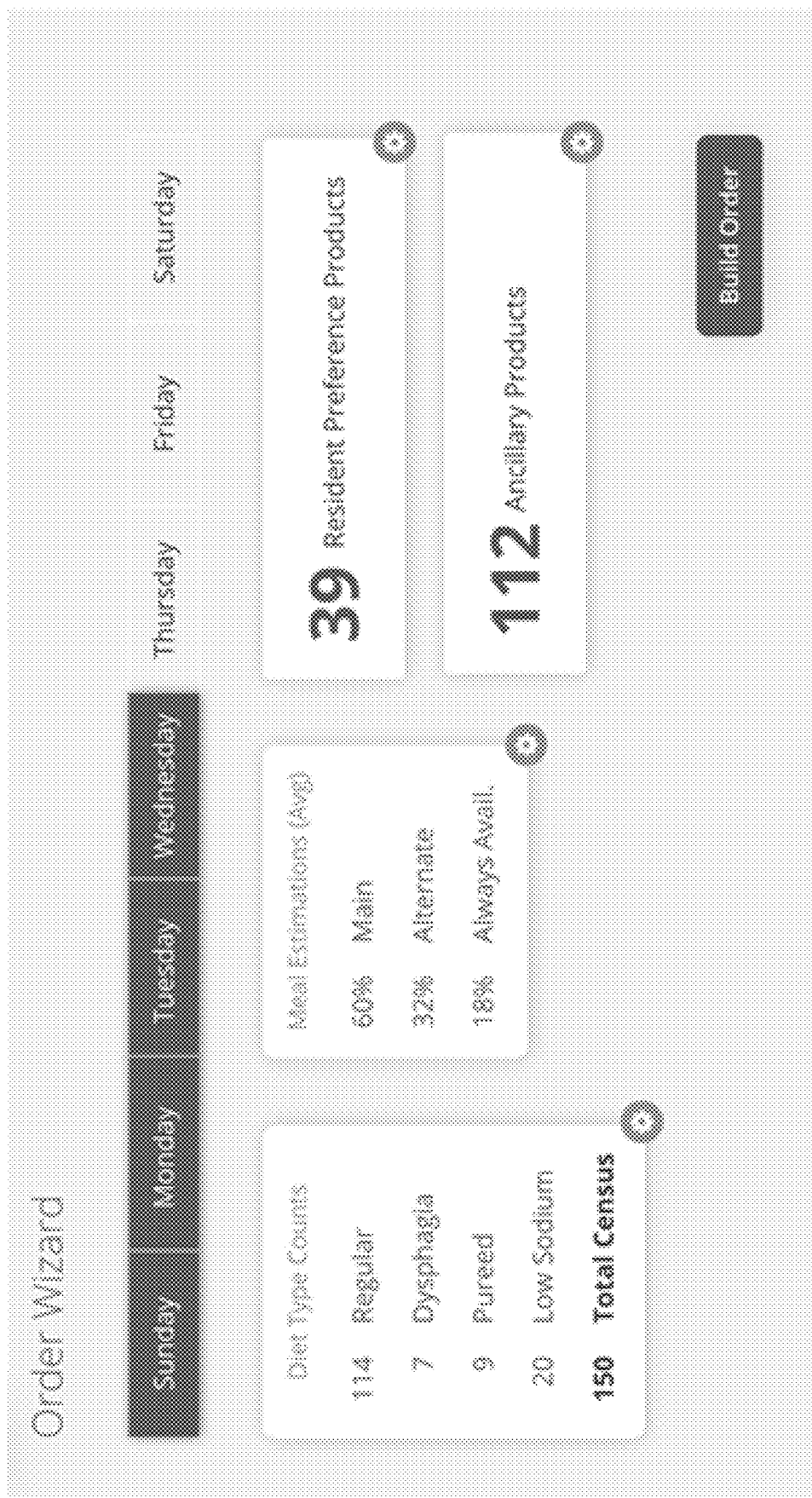
FIG. 19 shows an example of a portion of a user interface for presenting a facility summary in accordance with some embodiment of the disclosed subject matter.

At 914, process 900 can cause the facility summaries to be presented to the user for review. In some embodiments, process 900 can cause the facility summary for one or more facilities to be presented to a user for review, which can allow the user to quickly ascertain the state of the diets in place across the facility. The user can utilize the summary determine whether changes to overall menus or recipe selections are warranted. For example if a certain diet type exceeds the regular diet count, the user can determine that it would be preferable to change that diet type to the main serving. As another example, if alternative meal selection is growing compared to main meal selection, it could indicate to the user that the main meal recipes need to be adjusted or changed to align more with patient preferences. The review can also be used by the user to determine if ingredient orders are appropriate for the diet types at the facility, as changes in patient census can dynamically change the diet types present in the facility, altering the ingredients needed resulting in over or under ordering of certain ingredients. Such changes can be indicated in the review and can prompt the user to adjust ingredient ordering. FIGS. 19 and 20 show examples of different types of facility summaries that can be presented to a user in a user interface, with the summary of FIG. 20 including recommendations that have been identified for various patients, and the summary of FIG. 19 showing food service information across one particular facility.

At 916, process 900 can generate recommendations for each facility using models (e.g., trained machine learning models, algorithm-based optimizer models). In some embodiments, such recommendations can be for individual patients and/or across an entire facility. For example, as described above in connection with 714 of FIG. 7, recommendations for individual patients can be made with the focus on driving better outcomes for the patient. In such an example, such a recommendation can be a recommendation to adjust the patient's diet to a new type of diet (e.g., an adjustment to a new medical nutrition therapy diet) that is better suited to the patient's condition, or by adjusting the patient's diet to better correspond to the patient's preferences without necessarily making changes to the overall diet plan (e.g., by selecting ingredients and/or recipes that the patient has indicated through expressed feedback and/or behavior to have a preference for, and/or not selecting ingredients and/or recipes that the patient has indicated through expressed feedback and/or behavior to have an aversion to).

As another example, process 900 can generate facility recommendations with a focus on control costs, reducing waste, and/or otherwise improving the operations of the facility. For example, process 900 can recommend (e.g., via models 130) that a facility that has been purchasing gluten-free grains or starches adjust its purchases due to a change in census that led to fewer patients that require gluten-free ingredients. As another example, process 900 can recommend (e.g., via models 130), for the same facility, recipes with high patient preference that utilize the glute-free ingredients that are currently in inventory and that will no longer be needed for inclusion in the regular menu for all residents to draw down the existing supply of gluten-free ingredients, which would reduce waste and reduce the need to purchase non gluten-free ingredients until the gluten-free ingredients were used up.

At 918, process 900 can cause the recommendations to be presented to the user, and can receive instructions in light of the recommendations. In some embodiments, the recommendations can be presented in the form of changes to one or more of the menu for the facility (e.g., the order of meals in a cyclic menu), the recipe selection (e.g., for specific meals), and/or ingredients (e.g., components used in preparing the meal using a particular recipe). Additionally, in some embodiments, recommendations can be presented as draft instructions to be conveyed to staff members of the facility. For example, such instructions can include instructions to food service staff that include directions on alternative serving methods of recipes or ingredients, directions on alternative preparations of ingredients or recipes. As another example, such instructions can include suggestions on how to change ordering behaviors to reduce waste or maximize efficiency of ingredient usage.

At 920, process 900 can cause orders and/or recommendations to be presented to an interdisciplinary facility team, including the user, for discussion regarding how the recommended actions could potentially improve operations, patient outcomes, or other metrics. For example, process 900 can automatically schedule a video conference to discuss the recommendations, and provide the recommendations as a presentation that the user is prompted to present during the video conference.

Figure 10:
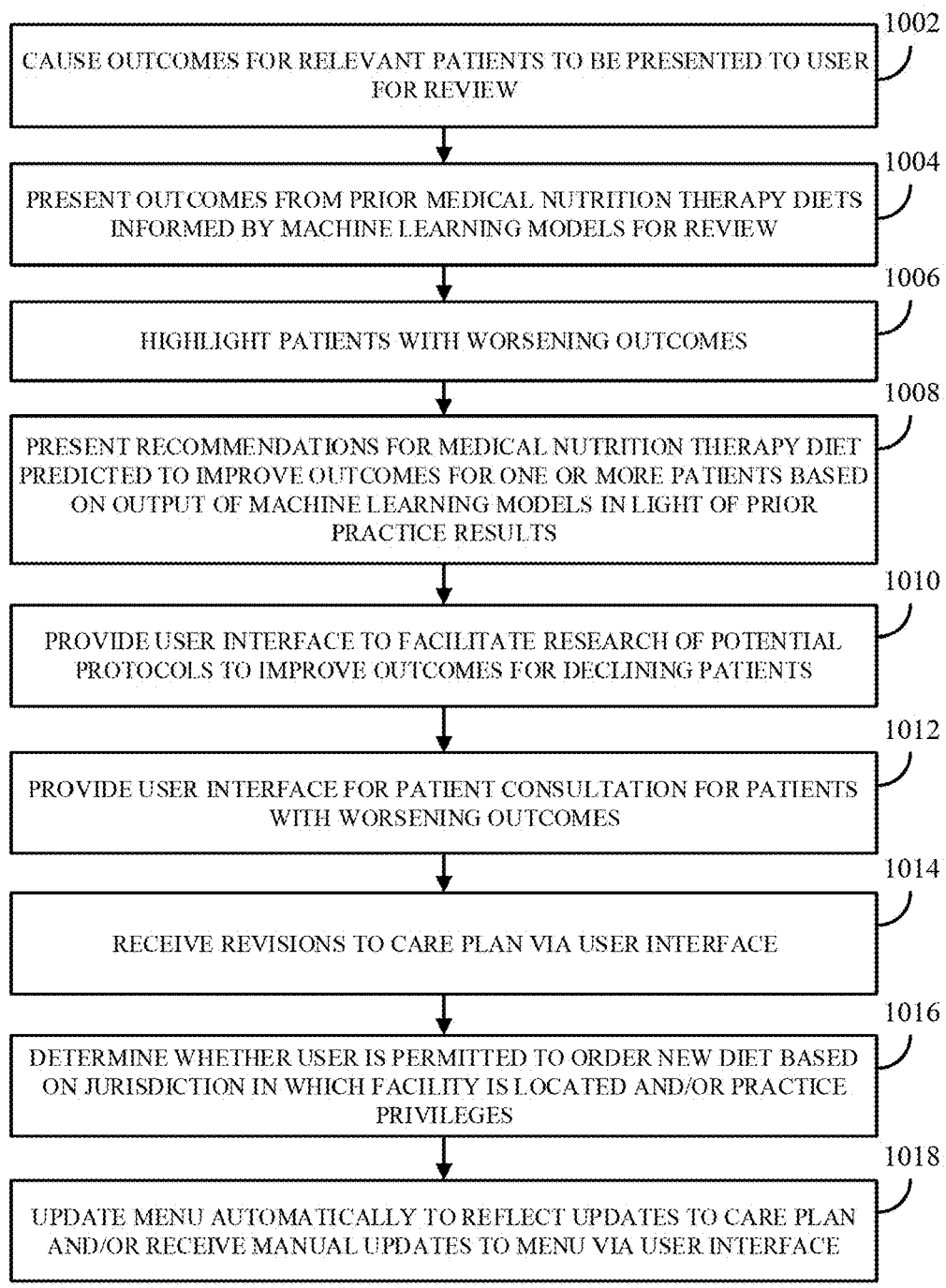
FIG. 10 shows an example of a process for facilitating medical nutrition therapy planning to improve patient outcomes in accordance with some embodiments of the disclosed subject matter.

FIG. 10 shows an example of a process for facilitating medical nutrition therapy planning to improve patient outcomes in accordance with some embodiments of the disclosed subject matter. At 1002, process 1000 can cause outcomes relevant to patients to be presented to a user (e.g., a registered dietitian) for review. For example, when a user is assigned a facility, outcomes associated with patients or residents at the facility can be presented to the user as part of a workflow of performing actions associated with the facility. For example, when a user is assigned a group of patients, outcomes associated with the patients can be presented to the user as part of a workflow of performing actions associated with the patients.

At 1004, process 1000 can cause the outcomes from prior medical nutrition therapy diets informed by models (e.g., trained machine learning models, algorithm-based optimizer models) to be presented for review for each patient identified at 1002. In some embodiments, the outcomes can be presented using any suitable technique or combination of techniques. For example, in some embodiments, outcomes can be presented based on a patients' diagnosis, and the patient's weight over time compared to the patients expected weight output by a model.

At 1006, process 1000 can highlight patients with worsening outcomes. In some embodiments, process 1000 can identify patients with worsening outcomes using any suitable technique or combination of techniques. For example, patients that are losing weight when the patient is on a diet that is intended to increase or maintain weight can be identified as patients with worsening outcomes. As another example, patients that are gaining significant amounts of weight when the patient is on a diet that is intended to decrease or maintain weight can be identified as patients with worsening outcomes.

At 1008, process 1000 can present recommendations for medical nutrition therapy diets predicted to improve outcomes for one or more patients based on an output of a model in light of prior practice results. For example, a patient's prior diet and vital statistics (e.g., weight over time) can be provided as input to a model, and the model can identify a diet that is predicted to produce a better outcome for the patient.

At 1010, process 1000 can provide a user interface to facilitate research of potential protocols to improve outcomes for declining patients. For example, in some embodiments, process 1000 can provide the recommendations at 1008, and links to resources that can be searched by the user for other protocols that may be appropriate given the patient's diagnosis and past history.

At 1012, process 1000 can provide a user interface that prompts the user to perform a patient consultation for patients with worsening outcomes, and can populate the user interface using information received from a menu system and/or electronic health record system (e.g., in response to the queries submitted as described above in connection with 706 and/or 708 of FIG. 7). In some embodiments, at least a portion of the user interface can be generated by practice control system 110, such as content used to populate at least a portion of the user interface, and another portion of the user interface can be generated by computing device 102 using an application being executed by the computing device.

At 1014, process 1000 can receive one or more revisions to a care plan for a patient via the user interface provided at 1010 and/or 1012. For example, the user can provide input based on the recommendations at 1008 and/or research performed at 1012 to update the care plan to include a protocol that is intended to improve the patient's outcomes.

At 1016, process 1000 can determine whether the user is permitted to order a new diet for the patient based on the jurisdiction in which the patient is located, the jurisdiction in which the facility caring for the patient is located, and/or whether the user has practice privileges at the facility. If process 1000 determines that the user is permitted to order the new diet (e.g., the jurisdiction allows a registered dietitian to order a diet if the registered dietitian has practice privileges at the facility, and both conditions are satisfied), process 1000 can submit a new diet order to the patient's electronic health records, a menu system, and/or a food service system. Otherwise, if process 1000 determines that the user is permitted to order the new diet themselves, process 1000 can submit a new diet for validation by a designated medical provider (e.g., a physician, a physician assistant, a nurse practitioner, or the like) upon which the new diet can be submitted to patient's electronic health records, a menu system, and/or a food service system.

At 1018, process 1000 can update a menu automatically (e.g., in a menu system, in a food service system) to reflect updates to the care plan, and/or can receive manual updates via a user interface. In some embodiments, updates provided at 1000 can ensure that the patient begins receiving appropriate food to meet the specifications of the newly ordered diet as soon as possible.

Figure 11:
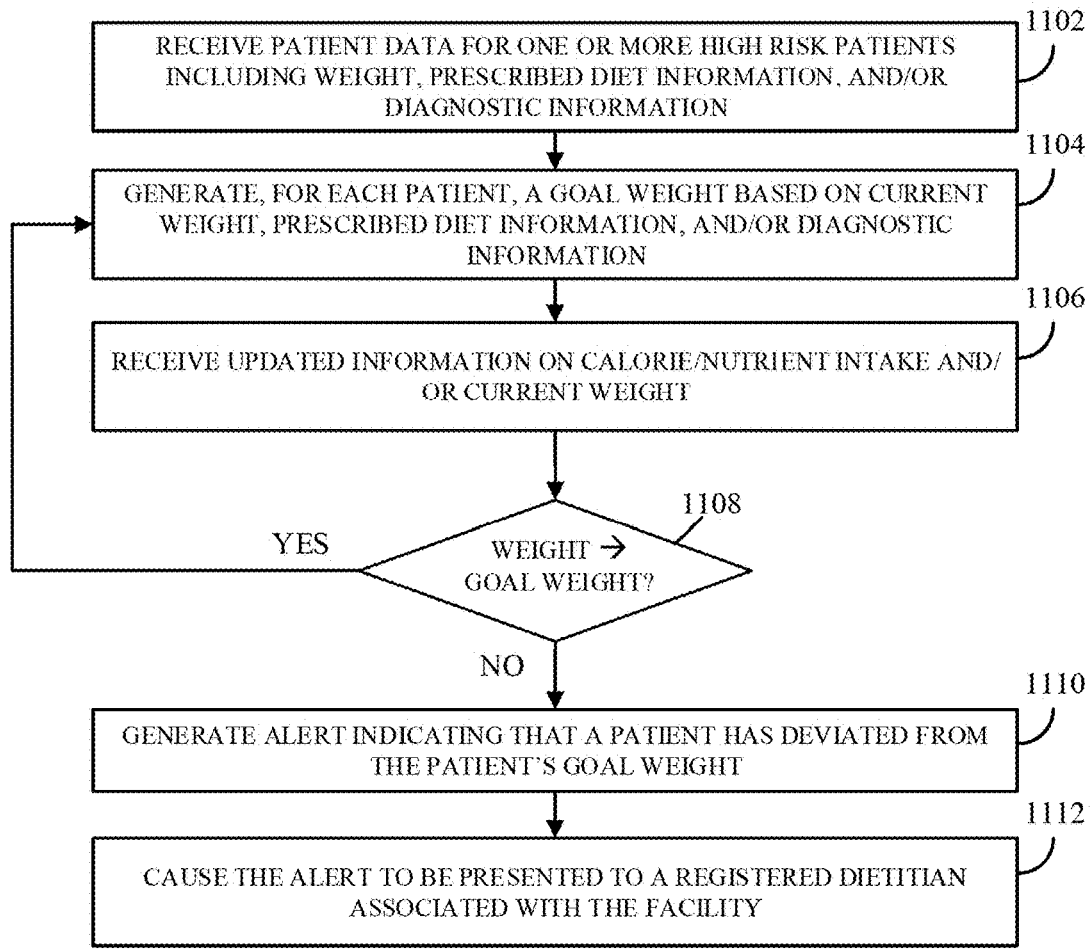
FIG. 11 shows an example of a process for automatically monitoring the dietary progress of high risk patients associated with a healthcare facility in accordance with some embodiments of the disclosed subject matter.

FIG. 11 shows an example 1100 of a process for automatically monitoring the dietary progress of high risk patients associated with a regulated facility in accordance with some embodiments of the disclosed subject matter. At 1102, process 1100 can receive patient data for one or more high risk residents and/or patients. The patient data can include a current weight, past weight measurements, whether the patient has been prescribed a particular diet type (e.g., a particular type of therapeutic diet), which diet type (if any) the patient has been prescribed, and/or diagnostic information related to a medical condition of the patient (e.g., a diagnosis, a prognosis, and the like).

At 1104, process 1100 can generate, for each patient, a goal weight based on the patient's current weight, prescribed diet information, and/or diagnostic information. In some embodiments, the goal can be for the patient to maintain weight, gain weight, or lose weight. In some embodiments, goal weights can be provided as user input and/or suggested and reviewed as part of a patient consultation and a diet development process (e.g., as described above in connection with FIG. 7).

At 1106, process 1100 can receive updated information regarding the calorie and/or nutrient intake of the patient and/or a current weight of the patient. In some embodiments, the calorie information can be based on input provided by one or more employees of the facility, by the patient, by a device (e.g. a scale that weighs a plate of food served to the patient before and after a meal time), and/or from any other suitable source. In some embodiments, the patient's current weight can be received from any suitable source. For example, the current weight can be retrieved from or received from an electronic medical record system associated with the patient (e.g., the weight can be input into the electronic medical record system by a medical professional such as a nurse or doctor. As another example, the current weight can be based on input to a user interface associated with a location database. As yet another example, the current weight can be received from a connected device, such as a smart scale (e.g., integrated in a pad under the patient's mattress).

At 1108, process 1100 can determine if the patient's current weight is appropriately trending toward the patient's goal weight and/or remaining within an acceptable weight range with acceptable variation (e.g., without moving more than a predetermined amount between measurements, which may indicate that the patient is trending unacceptably away from the goal weight) if the patient was already near the goal weight. If the patient's weight is trending toward the patient's goal weight (and/or not trending too far in the wrong direction) ("YES" at 1108), process 1100 can return to 1104 to determine whether the goal weight is still appropriate given the patient's current weight and health. Otherwise, if the patient's weight is diverging from the patient's goal weight and/or is not a trend to achieve the patient's goal weight within a particular amount of time ("NO" at 1108), process 1100 can move to 1110.

At 1110, process 1100 can generate an alert indicating that a patient has deviated from the patient's goal weight by at least a threshold amount.

At 1112, process 1100 can cause the alert to be presented to a registered dietitian associated with the facility. Additionally or alternatively, in some embodiments, the alert can be presented to a medical practitioner associated with the patient, such as a nurse or doctor.

Note that while process 1100 was described in terms of monitoring patient weight to determine whether to trigger generation of an alert that will cause the patient to be re-evaluated, this is merely an example. In some embodiments, in addition to, or in lieu of, monitoring patient weight, other metrics related to patient health can be monitored in order to trigger an alert that will cause the patient to be re-evaluated. For example, an average blood glucose level and/or A1C level can be generated for a diabetic or pre-diabetic patient at 1104, and can monitored at 1106 based on updates received from the patient's electronic health records. In such an example, if the patients average blood glucose and/or A1C is trending away from a goal level at 1108, process 1100 can generate an alert at 1110, and cause the alert to be presented at 1112.

Other examples of metrics that can be monitored to determine whether to trigger an alert can include cholesterol levels, blood pressure, triglycerides, ejection fraction, and many other metrics associated with various health conditions that can be affected by diet.

Figure 12:
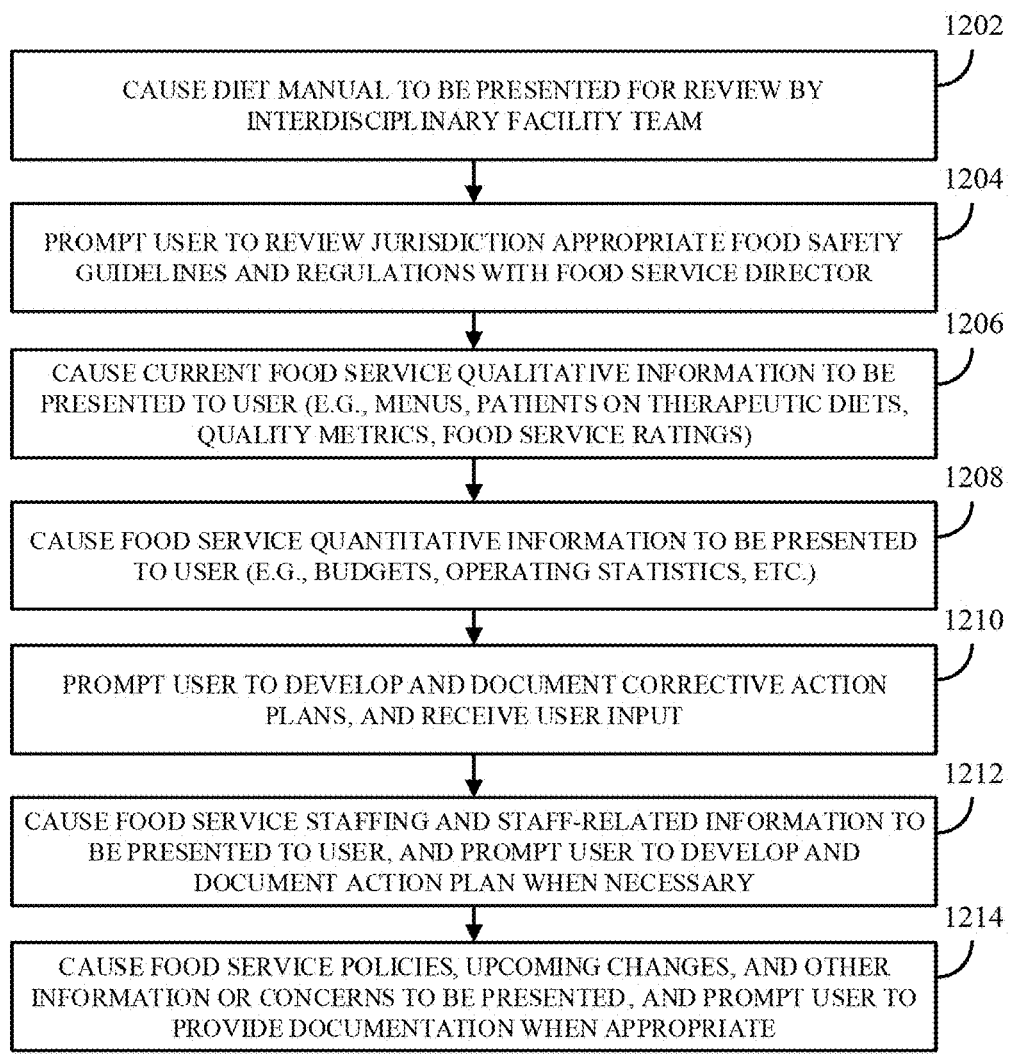
FIG. 12 shows an example of a process for facilitating food service management at healthcare facilities in accordance with some embodiments of the disclosed subject matter.

FIG. 12 shows an example of a process for facilitating food service management at healthcare facilities in accordance with some embodiments of the disclosed subject matter. At 1202, process 1200 can cause a diet manual to be presented for review by an interdisciplinary facility team, including a registered dietitian assigned to a facility. In some embodiments, a practice control system (e.g., practice control system 110) can create a conference or video conference periodically and add it to a calendar of appropriate team members to insure that the diet manual is reviewed at appropriate intervals.

At 1204, process 1200 can prompt the user assigned to the facility to review jurisdiction appropriate food safety guidelines with the food service director of the facility. In some embodiments, documenting regular meetings to go over such guidelines can provide evidence to regulators that the facility is using best practices in its food preparation and storage.

At 1206, process 1200 can cause current food service qualitative information to be presented to the user, such as the menus being served to residents and/or patients, the number of patients on various types of diets, quality metrics (e.g., based on reviews by residents and/or patients, based on reviews by supervisors), and food service ratings. In some embodiments, presenting such qualitative information can inform the user regarding the quality of the food service provided by a particular facility, which can have an impact on outcomes, as a poorly prepared diet or a menu lacking sufficient variety is more likely to lead to poor outcomes all else being equal.

At 1208, process 1200 can cause food service quantitative information to be presented to the user, such as budget information, operating statistics, and the like. In some embodiments, presenting such quantitative information can inform the user regarding how the resources that are allocated to food service are being used, and whether the use is being translated into quality.

At 1210, process 1200 can prompt the user to develop and document corrective action plans, if necessary, and can receive user input reflecting such plans. In some embodiments, the user can evaluate the performance of the food service based on the information presented at 1206 and/or 1208, and can determine whether corrective action is necessitated. If so, the user can develop an action plan.

At 1212, process 1200 can cause food service staffing and staff-related information to be presented to the user, and can prompt the user to develop and document an action plan when necessary. For example, a registered dietitian may be responsible for food service operations as part of the registered dietitian's job functions, and may thus be responsible for developing and implementing plans to help the facility comply with applicable regulations and/or guidelines (e.g., practice guidelines set by the Academy of Nutrition and Dietetics).

At 1214, process 1200 can cause food service policies, upcoming changes, and other information or concerns (e.g., raised by residents and/or patients) to be presented periodically, and can prompt the user to provide document where appropriate.

Figure 13:
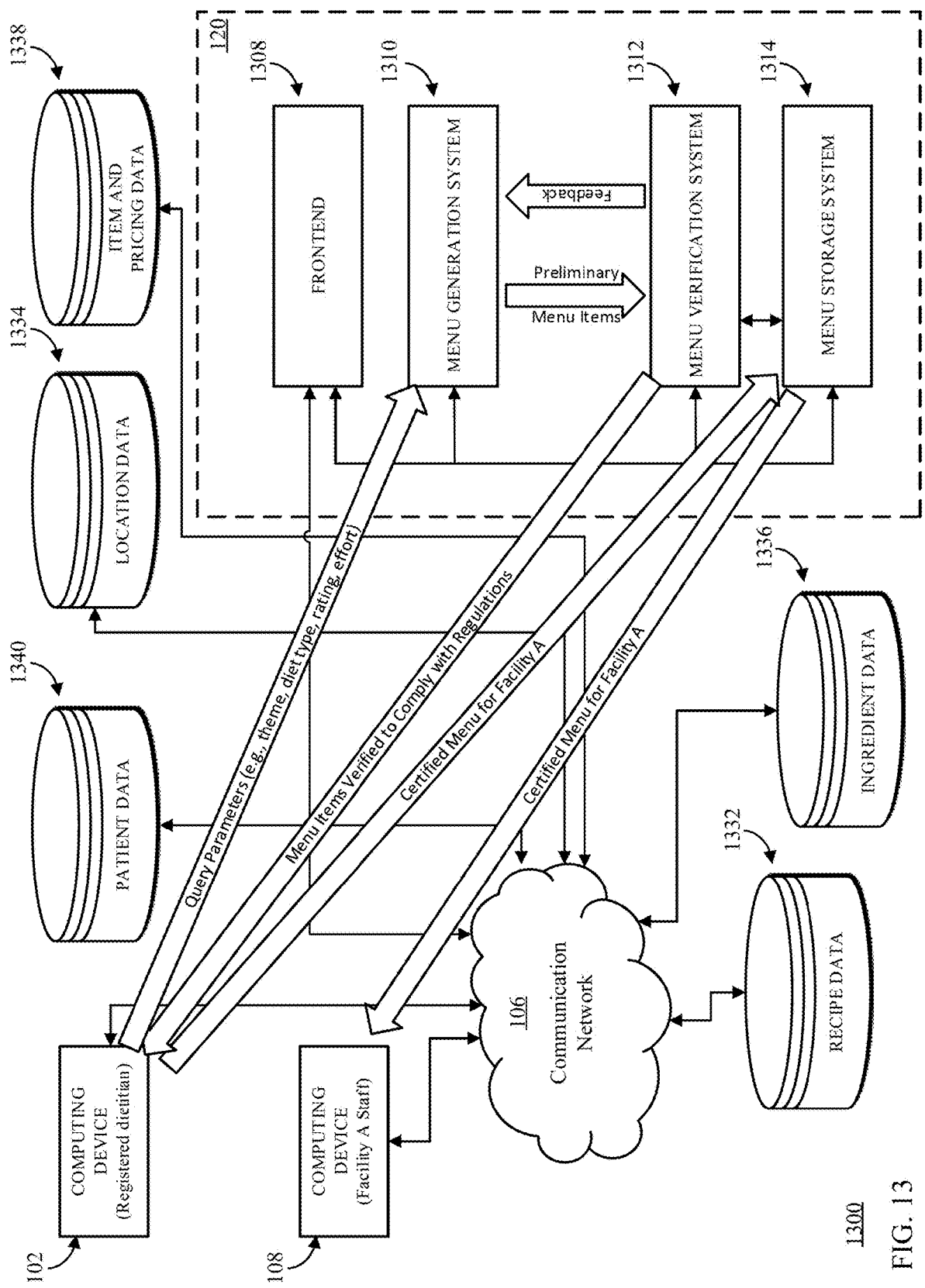
FIG. 13 shows an example of a system for automated dietary management in healthcare facilities in accordance with some embodiments of the disclosed subject matter.

FIG. 13 shows an example 1300 of a system for automated dietary management in healthcare facilities in accordance with some embodiments of the disclosed subject matter. In some embodiments, system 1300 can include a computing device 102 that can be utilized (e.g., by a registered dietitian) to interact with a menu system 120 via a communication network 106. In some embodiments, computing device 102 can be any suitable computing device or combination of computing devices. For example, compute device 102 can include physical computing devices associated with a user (e.g., a personal computer, a laptop computer, a server, a smartphone, a tablet computer, a wearable computer, and the like), and virtual computing devices provided through a compute service (e.g., via one or more virtual machines). In some embodiments, computing device 102 can be provided by an employer or an organization that retains the services of a user (e.g., a registered dietitian) of computing device 102 as an independent contractor. For example, computing device 102 can be a personal computer, a laptop computer, a tablet computer, a smartphone, a virtual machine, one or more containers, and the like, that is associated with a particular facility. For example, computing device 102 can be supplied by an organization that owns and/or operates menu system 120 and/or practice control system 110. In such an example, the organization can control which applications are installed on computing device 102, and/or can control which user or users are provided with credentials that facilitate use of computing device 102. In some embodiments, the organization can install or facilitate installation of one or more applications (e.g., mobile applications, or desktop applications) on computing device 102 that can be used to interact with menu system 120. Additionally or alternatively, in some embodiments, the organization can facilitate access to one or more application (e.g., web applications) by computing device 102 by providing credentials and/or a process for obtaining credentials to a user of computing device 102. For example, computing device 102 can be used to submit query parameters such as a theme, amount of effort, rating, and the like, that can be used when generating a menu.

In some embodiments, computing device 102 can be a device that is owned by a user, such as a registered dietitian. In such an example, the organization can facilitate the owner of the device in installing an application (e.g., as a mobile application, or a desktop application) or accessing an application (e.g., a web application) that can be used to interact with menu system 120.

In some embodiments, computing device 102 can interact with menu system 120 to provide one or more queries, feedback, and/or any other suitable input that can be used by the menu system during automated and semi-automated creation of a menu for a facility. For example, computing device 102 can submit credential information to frontend 1308 of menu system 120 that can be used to verify that a user of computing device 102 is permitted to utilize menu system 120. As another example, computing device 102 can submit query parameters to frontend 1308 of menu system 120, which can be used by menu system 120 when generating a menu. As yet another example, computing device 102 can provide feedback and/or other input to frontend 1308 of menu system 120 to make revisions to a menu that was automatically created by menu system 120.

In some embodiments, computing device 102 can submit a request for information from menu system 120 via frontend 1308. In some embodiments, frontend 1308 can request credential information from computing device 102 prior to providing information. For example, frontend 1308 can redirect computing device 102 to a user interface that prompts a user to enter or otherwise provide credential information. Note that in some embodiments, a user interface presented by computing device 102 can be generated by menu system 120 and/or computing device 102. For example, a user interface can be generated based on instructions (e.g., HTML code, JavaScript, and the like) provided to computing device 102 by a web server that implements at least a portion of frontend 1308. In such an example, the instructions can be used by an application being executed by computing device 102 (e.g., a general purpose application such as a web browser, or a special purpose application such as an application associated with menu system 120 that implements a portion of frontend 1308) to present the user interface. As another example, a user interface can be generated based on instructions generated by an application installed on and/or being executed by computing device 102 (e.g., a specialized application such as an application associated with menu system 120 that implements a portion of frontend 1308). In some embodiments, the user interface presented by computing device 102 can be populated using data provided by menu system 120 and/or any other system (e.g., a database housed outside of menu system 120, which can be a third party database that is maintained by an organization that is not associated with menu system 120). For example, in some embodiments, computing device 102 can access data about locations for which a user of computing device 102 is responsible from a location database 1334 maintained by an organization that owns and/or operates the locations.

In some embodiments, system 1300 can include computing device 108 associated with a facility for which a menu is being developed (e.g., by a user of computing device 102). For example, as described above in connection with FIG. 1, computing device 108 can be a personal computer, a laptop computer, a tablet computer, a smartphone, a terminal, a virtual machine, one or more containers, and the like, that is associated with a particular facility. For example, computing device 108 can be supplied by an organization that owns and/or operates the particular facility. In such an example, the organization can control which applications are installed on computing device 108, and/or can control which user or users are provided with credentials that facilitate use of computing device 108. In some embodiments, the organization can install or facilitate installation of one or more applications (e.g., mobile applications, or desktop applications) on computing device 108 that can be used to interact with menu system 120. Additionally or alternatively, in some embodiments, the organization can facilitate access to one or more application (e.g., web applications) by computing device 108 by providing credentials and/or a process for obtaining credentials to a user of computing device 108. For example, computing device 108 can be used to submit query parameters such as a theme, a diet type (e.g., low sodium, low fat) amount of effort, rating, and the like, that can be used when generating a menu.

In some embodiments, computing device 108 can be a device that is owned by an employee or other user associated with the facility. In such an example, the organization can facilitate the owner of the device in installing an application (e.g., as a mobile application, or a desktop application) or accessing an application (e.g., a web application) that can be used to interact with menu system 120. As another example, the organization can provide the owner of computing device 108 with access to a virtual machine controlled by the organization and/or an entity associated with menu system 120 that is configured to interact with menu system 120. In such an example, the organization can provide credentials to a user of computing device 108 that can be used to access the virtual machine, which can be configured to interact with system 120 with or without additional credentials.

In some embodiments, computing device 102 and/or computing device 108 can provide one or more query parameters and/or other parameters to a menu generation system 1310. In some embodiments, menu generation system 1310 can be configured to generate a menu of meals and/or snacks for each day of a particular period (e.g., a day, multiple days, a week, two weeks, a month, and so on) that satisfy, individually and collectively, particular requirements imposed by one or more entities.

For example, the organization and/or the facility can impose certain constraints on an organizational, facility, and/or individual resident/patient level to be met by the menu system 120 which can be taken into account by menu generation system 1310. In a more particular example, a target number of courses and/or calories in each meal and/or each day (or other period) can be a constraint that is provided by the organization, facility, and/or other party (e.g., a registered dietitian associated with the facility).

As another more particular example, a maximum allowable cost per day per resident/patient can be a constraint that is provided by the organization and/or facility. In such an example, the maximum allowable cost can vary based on the facility and/or on a per resident/patient level. A resident on a special type of diet may be associated with a higher maximum cost per day which may be required in order to satisfy the requirements of that special diet.

As yet another more particular example, information identifying special dietary rules to apply to the organization as a whole, to one or more particular facilities as a whole, and/or to specific residents/patients can be a constraint that is provided by the organization and/or facility. In such an example, the special dietary rules can be rules that are followed based on personal preference (e.g., the organization, facility, and/or specific residents/patients can be designated as following Kosher dietary rules, Halal dietary rules, vegetarian dietary rules, vegan dietary rules, and the like) and/or can be rules that are followed as part of a particular diet (e.g., a particular type of therapeutic diet, a medical nutrition therapy diet, a diet that complies with one or more particular restrictions) recommended and/or prescribed by a medical practitioner and/or registered dietitian (e.g., a low sodium diet, a diabetic diet, a calorie controlled diet, a low fat and/or cholesterol diet, a high fiber diet, a renal diet, a puree diet, a food allergy diet, a diet that includes supplemental meals, calories and/or nutrients, and the like).

As still another more particular example, information identifying cultural rules to apply to the organization as a whole, to one or more particular facilities as a whole, and/or to specific residents/patients can be a constraint that is provided by the organization and/or facility. In such an example, diet may vary based on the location of the facility and/or cultural background of one or more residents and/or patients. The types of foods and/or flavors eaten at different meals may vary widely between cultures, such that a food that is often consumed as a dinner or snack item in one food culture may be consumed as a breakfast item in another.

In some embodiments, menu generation system 1310 can use one or more constraints (e.g., constraints described above) when selecting and/or scheduling meals and/or snacks for each day. In some embodiments, menu generation system 1310 can query a recipe database using one or more query parameters to identify recipes corresponding to meals that can be used to generate a menu for a particular facility. Additionally, in some embodiments, menu generation system 1310 can submit multiple queries using varying parameters to generate a suitable group of recipes. In some embodiments, query parameters can include a theme (e.g., corresponding to a keyword associated with particular types of recipes, such as seasonal (e.g., spring/summer, fall/winter, holiday), diet specific (e.g., mind, Mediterranean, DASH, keto), regional (e.g., Northeast, Midwest, Southern, Southwest), cultural/religious (e.g., Cuban, Kosher, Halal), fun, festive), a user rating (e.g., a user rating that is ostensibly based on enjoyment of food prepared using the recipe, clarity of the recipe, effort required to prepare the recipe, and any other factors that a user may consider when rating a recipe), an expert rating (e.g., a rating or ratings provided by a person having certain qualifications), diet type, a rated effort (e.g., in minutes, complexity) required to prepare the recipe, a type of recipe (e.g., entrée, side, appetizer, snack, dessert, and so on), and/or any other suitable parameter. In some embodiments, the number of meals, mealtimes, types of meals, and meal patterns can be defined to match what is specified in a diet manual, and can also be constrained to comply with regulations (e.g., CMS regulations).

In some embodiments, different types of menus can be generated using mechanisms described herein, including a cycle menu and a restaurant style menu. A cycle menu can specify a recipe that should be used for each meal for each day of the week for a specified period of time (e.g., in weeks). The recipe can then be used to specify recipe equivalents for each diet type (e.g., as shown in FIG. 4). In such a menu, generally only a single recipe is offered, sometimes with limited (e.g., a single) alternatives. A restaurant style, or always available menu, can be provided in which a patient can pick items a la carte. In such a menu, some items can be limited as available only during certain meals (e.g., breakfast, lunch, or dinner). In some embodiments, menu generation system 1310 can prompt a user to select a type of menu to be created (e.g., cyclic or restaurant style), a period of time that is to be covered by the menu (e.g., in weeks), meal times, and/or any other suitable information. In some embodiments, such information can be retrieved and/or imported from a diet manual.

In some embodiments, menu generation system 1310 can submit one or more queries to a recipe database 1332 to retrieve recipes that can be used to generate a menu for a particular facility. In some embodiments, menu generation system 1310 can use any suitable technique or combination of techniques to generate queries used to query recipe database 1332. In some embodiments, menu generation system 1310 can submit queries for recipes that are compliant with each type of diet type that the menu to be generated needs to accommodate. In some embodiments, menu generation system 1310 can submit queries with a specified skill rating or range of skill ratings, to ensure that the recipes returned by recipe database 1332 are well matched with the staff of the facility. In some embodiments, menu generation system 1310 can submit queries for different types of meals that will allow the facility to satisfy the meal pattern specified in the diet manual for the facility (if one exists). In some embodiments, generation system 1310 can submit queries for specific dishes that the customer would like to include (e.g., a dish that has been requested, a popular dish).

In some embodiments, menu generation system 1310 can receive recipes from recipe database 1332 in response to one or more queries. In some embodiments, the recipes can be received in any suitable format, such as a machine readable format, or a human readable format. For example, the recipes can be received as html files. As another example, the recipes can be received as xml files.

In some embodiments, menu generation system 1310 can select one or more recipes for each meal in a menu to be created using any suitable technique or combination of techniques. For example, in some embodiments, menu generation system 1310 can utilize one or more machine learning techniques to select recipes for each meal. In such an example, menu generation system 1310 can use a machine learning model that has been trained to select recipes that satisfy one or more constraints per meal, per day, and/or per resident, and/or that attempts to maintain variety in the menu to avoid serving the same meals repeatedly. As another example, menu generation system 1310 can utilize one or more algorithm-based optimizer models to select recipes for each meal. In such an example, menu generation system 1310 can use an algorithm-based optimizer model that has been configured to select recipes that satisfy one or more constraints per meal, per day, and/or per resident, and/or that attempts to maintain variety in the menu to avoid serving the same meals repeatedly In some embodiments, menu generation system 1310 can use a machine learning model or models that have been trained to tag recipes with information that can be used during item selections. For example, the machine learning model or models can be trained to tag a recipe based on meal type (e.g., breakfast, lunch, dinner, snack, side dish), whether a recipe meets a meal pattern defined by USDA (e.g., the recipe meets the definition of a snack, or lunch meal pattern defined by USDA), ingredient tags (e.g., identifying a protein in the recipe, which can help avoid repeating proteins), production difficulty (e.g., based on number of ingredients, number of steps, and/or tools needed to prepare the recipe), allergens, diet type (e.g., whether the recipe is expected to be part of a diet that is compliant with a particular type of diet, such as a particular type of therapeutic diet), special events (e.g., holiday meals, cookouts, birthday, Friday Fish Fry), and/or using any other suitable type of tag. Additionally or alternatively, in some embodiments, menu generation system 1310 can use an algorithm-based optimizer model or models that have been configured to tag recipes with information that can be used during item selections. For example, the algorithm-based optimizer model or models can be configured to tag a recipe based on meal type, whether a recipe meets a meal pattern defined by USDA, ingredient tags, production difficulty, allergens, diet type, special events, and/or using any other suitable type of tag.

In some embodiments, menu generation system 1310 can select one or more recipes for each meal in a menu to be created such that the recipes collectively satisfy a set of constraints. For example, a template can specify that each meal includes a particular set of ingredients. Table 1 provides an example of a template that can be used to supply a set of constraints to a menu created by menu generation system 1310. In addition to insuring that servings of particular types of ingredients are included with each meal, other constraints can also be applied, such as a rule prohibiting the same protein from being served at two consecutive meals, or the same fruit or vegetable from being served on two consecutive days. In some embodiments, menu generation system 1310 can calculate a frequency score such that recipe selections that would increase the frequency score of a particular ingredient with a relatively low frequency score (and a relatively high rating) are preferentially selected.

TABLE 1

| Day | Breakfast | Lunch | Dinner |
|---|---|---|---|
| 1 | 1 milk<br>1 fruit/vegetable<br>1 grain | 1 milk<br>2 fruit/vegetable<br>1 grain<br>1 meat | 1 milk<br>2 fruit/vegetable<br>1 grain<br>1 meat |
| 2 | 1 milk<br>1 fruit/vegetable<br>1 grain | Holiday Meal<br>1 milk<br>2 fruit/vegetable<br>1 grain<br>1 meat | 1 milk<br>2 fruit/vegetable<br>1 grain<br>1 meat |
| 3 | 1 milk<br>1 fruit/vegetable<br>1 grain | 1 milk<br>2 fruit/vegetable<br>1 grain<br>1 meat | Friday Fish Fry<br>1 milk<br>2 fruit/vegetable<br>1 grain<br>1 meat |

In some embodiments, menu generation system 1310 can interact with a menu verification system 1312 that can enforce one or more constraints. For example, menu generation system can make one or more preliminary recipe selections, and can provide the preliminary recipe selections to the menu verification system to determine whether one or more constraints (each of which may or may not have been taken into account by menu generation system 1310 during a recipe selection process) are satisfied. For example, menu verification system 1312 can determine whether requirements of federal, state, and/or local regulations are satisfied by the preliminary recipe selections. In such an example, if a particular meal and/or day does not satisfy the constraints, menu verification system 1312 can provide feedback related to the failure to satisfy one or more of the constraints to menu generation system 1310, which can use the feedback to adjust the recipe selections to satisfy one or more of the constraints.

In some embodiments, menu verification system 1312 can enforce constraints in a stepwise manner and/or can enforce the constraints collectively. For example, menu verification system 1312 can evaluate a set of one or more constraints to determine if the preliminary recipe selections received from menu generation system 1310 complies with the constraints. In such an example, if any of the constraints are not satisfied, menu verification system 1312 can provide feedback to menu generation system 1310 before evaluating any of the other constraints. As another example, menu verification system 1312 can evaluate the preliminary recipe selections received from menu generation system 1310 against all of the constraints that menu verification system 1312 is configured to enforce. In such an example, if at least one constraint is not satisfied, menu verification system 1312 can provide feedback indicating which constraints are not satisfied to menu generation system 1310.

In some embodiments, menu verification system 1312 can apply some constraints to individual meals that each correspond to one or more preliminary recipe selections, while other constraints can be applied to larger periods of time, such as one or more days. For example, menu verification system 1312 can apply a constraint related to minimum nutrition requirements or target calories for a particular meal (e.g., breakfast, lunch, dinner, and so on) imposed by one or more regulations to each meal individually. As another example, menu verification system 1312 can apply a constraint related to a maximum cost per resident/patient per day across all meals and/or recipes associated with a particular day.

In some embodiments, if menu verification system 1312 determines that a constraint is not explicitly satisfied, menu verification system 1312 can determine whether the preliminary recipe selections are within a threshold amount of a value associated with the constraint. For example, certain constraints (e.g., cost per day) may be more flexible than other constraints (e.g., whether a meal is in compliance with a particular diet type). In some embodiments, menu verification system 1312 and/or menu generation system 1310 can include recipes that do not explicitly comply with one or more constraints on a prospective menu to be reviewed by a registered dietitian (or other suitable reviewer), and can provide information indicating that one or more constraints are not satisfied by the menu. In such embodiments, the information can include and/or be associated with information indicating which of the constraints are not satisfied and how they are not satisfied. For example, if a solution cannot be found that satisfies two constraints simultaneously (e.g., cost per day and diet type), menu verification system 1312 and/or menu generation system 1310 can determine which of the constraints to satisfy, and can indicate to a user that the other constraint was not satisfied.

In some embodiments, menu system 120 (e.g., via menu generation system 1310 and/or menu verification system 1312) can identify specific items that the facility is likely to use to prepare a recipe based on the ingredients in the recipe using any suitable technique or combination of techniques. For example, if a recipe calls for four 4 ounce chicken breasts, menu system 120 can identify a particular chicken breast (e.g., by stock keeping unit (SKU)) that is likely to be ordered if the recipe is selected for inclusion in the menu for a particular facility. In some embodiments, menu system 120 can interact with an order management system to identify which items the facility is likely to order and/or have on hand to prepare the recipe. For example, menu system 120 can query the order management system for items included on an order guide (e.g., one or more general order guides and/or a facility order guide) associated with the facility. In such an example, menu system 120 can determine which item(s) (if any) from the order guide(s) correspond to an ingredient in the recipe.

In some embodiments, menu system 120 can query an item database (e.g., item and price database 1338) using identifying information of an ingredient from a recipe (e.g., a name of the ingredient), and the item database can return information identifying an item (e.g., by SKU) or items that are likely to be ordered by the facility and/or that the facility is likely to have on hand. In some embodiments, menu system 120 can query the item database (e.g., item and price database 1338) for all ingredients that may be needed to prepare each recipe.

In some embodiments, menu system 120 can query a patient database (e.g., patient database 1340) using identifying information of a patient, the patient database can return information about the patient that is maintained by facility and/or by one or more vendors in association with the patient. For example, the patient database can return information about the patient's current diet, meals (and/or snacks) ordered by the patient, meals (and/or snacks) prepared for and served to the patient, the patient's preferences (e.g., food preferences), dietary restrictions, a diet type(s) assigned to the patient, and/or any other suitable information about the patient. Additionally or alternatively, in some embodiments, the patient database can store and/or return patient health records and/or other protected health information.

In some embodiments, menu system 120 can query an ingredient database (e.g., ingredient database 1336) using any suitable identifying information (e.g., an SKU returned by the item database) of an item that is likely to be used to prepare the recipe. In some embodiments, the nutrition information can include any suitable information such as calories, protein, carbohydrates, fat, sugar, added sugar, fiber, sodium, /or various vitamins and/or minerals, and/or any other suitable nutrition information.

In some embodiments, menu system 120 (e.g., via menu generation system 1310 and/or menu verification system 1312) can use nutritional information about each item to determine a nutritional profile for each recipe. In some embodiments, menu system 120 (e.g., via menu generation system 1310 and/or menu verification system 1312), can determine whether the nutritional profile associated with a particular recipe is compliant with one or more constraints.

In some embodiments, menu system 120 (e.g., via menu generation system 1310 and/or menu verification system 1312) can determine a cost per serving (e.g., per person) for each recipe based on the prices of one or more items that a facility is likely to order. In some embodiments, menu system 120 (e.g., via menu generation system 1310 and/or menu verification system 1312) can query a pricing database (e.g., item and pricing database 1336) to determine a price associated with one or more items that are likely to be used to prepare the recipe. In some embodiments, the pricing data can be retrieved from an order management system, which can determine a price based on a list price charged by a distributor, and one or more contractual relationships between the organization/facility and the distributor and/or manufacturer of the item (e.g., discounts and/or rebates to which the organization/facility is entitled when ordering a particular item(s)). For example, the organization/facility may be entitled to a rebate on a particular brand of item based on a contractual relationship, which can be factored into a price provided to menu system 120.

In some embodiments, menu system 120 (e.g., via menu generation system 1310 and/or menu verification system 1312) can use pricing information about each item to determine a cost (e.g., per serving, per resident, total) associated with a recipe. In some embodiments, menu system 1304 (e.g., via menu generation system 1310 and/or menu verification system 1312), can determine whether the cost associated with a particular recipe is compliant with one or more constraints, such as a maximum cost per day.

In some embodiments, menu system 120 (e.g., via menu generation system 1310 and/or menu verification system 1312) can determine information about residents and/or patients for which a menu is being created. In some embodiments, menu system 120 (e.g., via menu generation system 1310 and/or menu verification system 1312) can query a location database (e.g., location database 1334) to determine various information about the facility for which a menu is being generated. For example, the information can include the number of residents and/or patients to be served at each meal and/or snack (e.g., sometimes referred to as the audience for the menu). As another example, the information can include information indicative of the number of and/or patients that are associated with various diet types (e.g., sometimes referred to as the diet spread for the facility). As yet another example, the information can include a maximum cost per day, which can be an aggregate parameter (e.g., for all people for a day, for a week) and/or an individual parameter (e.g., cost per resident/patient per day, cost per resident/patient per particular meal). In such an example, the maximum cost can vary by diet type in recognition that the costs associated with different diets may vary.

In some embodiments, menu generation system 1310 can make one or more adjustments to a proposed menu based on feedback received from menu verification system 1312. For example, menu verification system 1312 can indicate that a particular meal is not in compliance with a particular regulation, and menu generation system 1310 can adjust the recipe(s) associated with the meal to attempt to bring the meal into compliance with the regulation. In some embodiments, menu generation system 1310 and menu verification system 1312 can continue to make adjustments until the menu complies with all relevant constraints. Alternatively, in some embodiments, menu generation system 1310 and menu verification system 1312 can continue to make adjustments until the menu complies with a threshold number of constraints, or until a threshold number of adjustments have been made.

In some embodiments, menu generation system 1310 can generate a particular recipe or combination of recipes for each meal in a particular period of time, and can generate alternate sets of one or more recipes that can be substituted into a particular meal. In some embodiments, menu generation system 1310 can generate a separate menu and/or separate meal that complies with a particular constraint or set of constraints. For example, menu generation system 1310 can generate a separate menu that complies with kosher rules, a separate menu that complies with a particular type of diet (e.g., a particular type of therapeutic diet, a particular medical nutrition therapy diet), or a separate menu that complies both with kosher rules and a particular type of diet. In some embodiments, a proposed menu can include multiple choices for one or more meals. For example, if a particular facility offers residents/patients the chance to choose one or more dishes from a list of choices, the menu can include multiple different recipes that can be combined in various ways, such that the combinations satisfy the constraints (e.g., each combination of appetizer, entrée, side, and dessert that can be chosen satisfies a particular set of constraints).

In some embodiments, menu system 120 can provide (e.g., via a user interface presented by computing device 102) a proposed menu for adjustment and/or certification by a registered dietitian. For example, menu system 120 can cause a proposed menu generated by menu generation system 1310 and verification system 1312 to be presented by computing device 102. In some embodiments, a user of computing device 102 can interact with the user interface via computing device 102 to make one or more changes to the proposed menu. For example, a registered dietitian can substitute one set of recipes for another, add or delete recipes from a particular meal, manually adjust the ingredients used in a particular recipe, manually search for a recipe to add to the menu (e.g., as an addition and/or a substitute). In some embodiments, menu system 120 can provide feedback as a user of computing device 102 makes changes to indicate whether an updated menu complies with all of the constraints, with more constraints than the proposed menu, with fewer constraints than the proposed menu, and so on.

In some embodiments, a user of computing device 102 can provide a certification indicating that a particular menu or combination of menus are appropriate for the residents and/or patients of the facility for which the menu is being generated. In some embodiments, the certification can be accepted if the user has provided credentials associated with a particular registered dietitian (or other appropriate user), and/or the user can be prompted to enter credentials during the certification process to verify that the user has the authority to certify the main.

In some embodiments, a certified menu can be stored in a menu storage system 1314 that can include a database that is configured to store one or more menus. In some embodiments, information stored by menu storage system 1314 can be accessed by a user of computing device 108 to, for example, plan out a menu for a facility, order items for a facility that can be used to prepare meals based on the menu, and so on. For example, computing device 108 can interact with menu storage system 1314 (e.g., via frontend 1308) to populate a user interface that can be used to review a menu for a particular period of time.

In some embodiments, recipe database 1332 can include any suitable information that is organized in any suitable manner. In some embodiments, recipe database 1332 can include recipes that can be used to prepare various foods. Each recipe can be associated with ingredients used to prepare the food, and instructions for preparing the food. In some embodiments, recipe database 1332 can include metadata related to each recipe, such as one or more keywords associated with the recipe, a user rating, an expert rating, an effort rating, one or more themes, one or more tags indicating that the recipe is a particular type of recipe (e.g., vegan, kosher, and the like), one or more tags indicating that the recipe is appropriate for inclusion in a particular type or types of diet, one or more tabs indicating a meal for which the recipe is appropriate (e.g., breakfast, lunch, snack, and so on), and/or any other suitable metadata associated with the recipe.

In some embodiments, recipe database 1332 can be maintained as part of menu system 120 and/or can be maintained separately (e.g., by a third party) and used by menu system 120. In some embodiments, system 1300 can include multiple recipe databases 1332 which can be maintained by different entities, and which can include different (e.g., overlapping or non-overlapping) collections of recipes.

In some embodiments, location database 1334 can include any suitable information that is organized in any suitable manner. In some embodiments, location database 1334 can include information about facilities associated with users of menu system 120. In some embodiments, location database 1334 can be populated at least in part from an electronic medical records system associated with one or more facilities. For example, the electronic medical records system can be used to populate the number of residents of a facility. As another example, the electronic medical records system can be used to indicate how many residents of a facility are on a particular diet type. In some embodiments, information about residents can be aggregated and/or anonymized in location database 1334 in order to comply with one or more regulations that limits the use of personal health information (e.g., one or more regulations based on the Health Insurance Portability and Accountability Act of 1996). Additionally or alternatively, in some embodiments, information about one or more facilities can be updated based on input received from a user (e.g., a user of computing device 108).

In some embodiments, location database 1334 can be maintained as part of menu system 120 and/or can be maintained separately (e.g., by a third party) and used by menu system 120. In some embodiments, system 1300 can include multiple location databases 1334 which can be maintained by different entities, and which can include information about different organizations.

In some embodiments, ingredient database 1336 can include any suitable information that is organized in any suitable manner. In some embodiments, ingredient database 1336 can include information about one or more items that can be used as ingredients in recipes, such as nutritional information. In some embodiments, ingredient database 1336 can be maintained as part of menu system 120 and/or can be maintained by separately (e.g., by a third party) and used by menu system 120. In some embodiments, system 1300 can include multiple ingredient databases 1336 which can be maintained by different entities, and which can include information about different organizations.

In some embodiments, item and pricing database 1338 can include information about items that can be ordered by various facilities and/or information about a price associated with the items. In some embodiments, item and pricing database 1338 can be maintained as part of an order management system and/or can be populated using information from an order management system. In some embodiments, the order management system can be used by an organization and/or facility to harmonize procurement activities from one or more distributors. For example, the order management system can be used to generate an order guide that can be associated with the facility and used to populate a user interface of an order procurement system.

In some embodiments, item and pricing database 1338 can be maintained as part of menu system 120 and/or can be maintained separately (e.g., by a third party) and used by menu system 120. In some embodiments, system 1300 can include multiple item and pricing database 1338 which can be maintained by different entities, and which can include information about different organizations. In some embodiments, ingredient database 1336 and item and pricing database 1338 can be combined and maintained as a single database.

In some embodiments, patient database 1340 can include information about patients associated with the facility. In some embodiments, patient database 1340 can be maintained as part of an electronic health record system and/or can be populated using information from an electronic health record system. In some embodiments, the electronic health record system can be used by an organization and/or facility to securely store and maintain protected health information about patients at the facility. In some embodiments, patient database 1340 can be used to securely store and maintain information that may not be considered protected health information about patients. In some embodiments, any suitable information about patients can be stored using patient database 1340, such as information about the patient's current diet (e.g., a medical nutrition therapy diet that has been developed for the patient, which may or may not be associated with a particular type of diet), meals (and/or snacks) ordered by the patient in the past, meals (and/or snacks) prepared for and served to the patient in the past, the patient's expressed and/or revealed preferences (e.g., food preferences), dietary restrictions (e.g., associated with a particular type of diet assigned to the patient, associated with the medical nutrition therapy diet developed for the patient, inherent to the patient such as an allergy or sensitivity, ordered by a medical practitioner, etc.), future meals planned for the patient, and/or any other suitable information about the patient.

In some embodiments, patient database 1340 can be maintained as part of menu system 120 and/or can be maintained separately (e.g., by a third party) and used by menu system 120. In some embodiments, system 1300 can include multiple patient databases 1340 which can be maintained by different entities, and which can include information about different patients, and/or can include different types of information about the same patients.

Note that, in some embodiments, information stored in recipe database 1332, location database 1334, ingredient database 1336, item and pricing database 1338, and/or patient database 1340 can be stored in a distributed database and/or distributed record that is maintained across various computing devices in a network of computing devices. For example, in some embodiments, such data can be stored using blockchain techniques to store and update data in an encrypted and distributed record. As another example, such data can be stored using a secured and encrypted database (e.g., implemented using relational and/or non-relational data stores) to securely store and update data.

Figure 14:
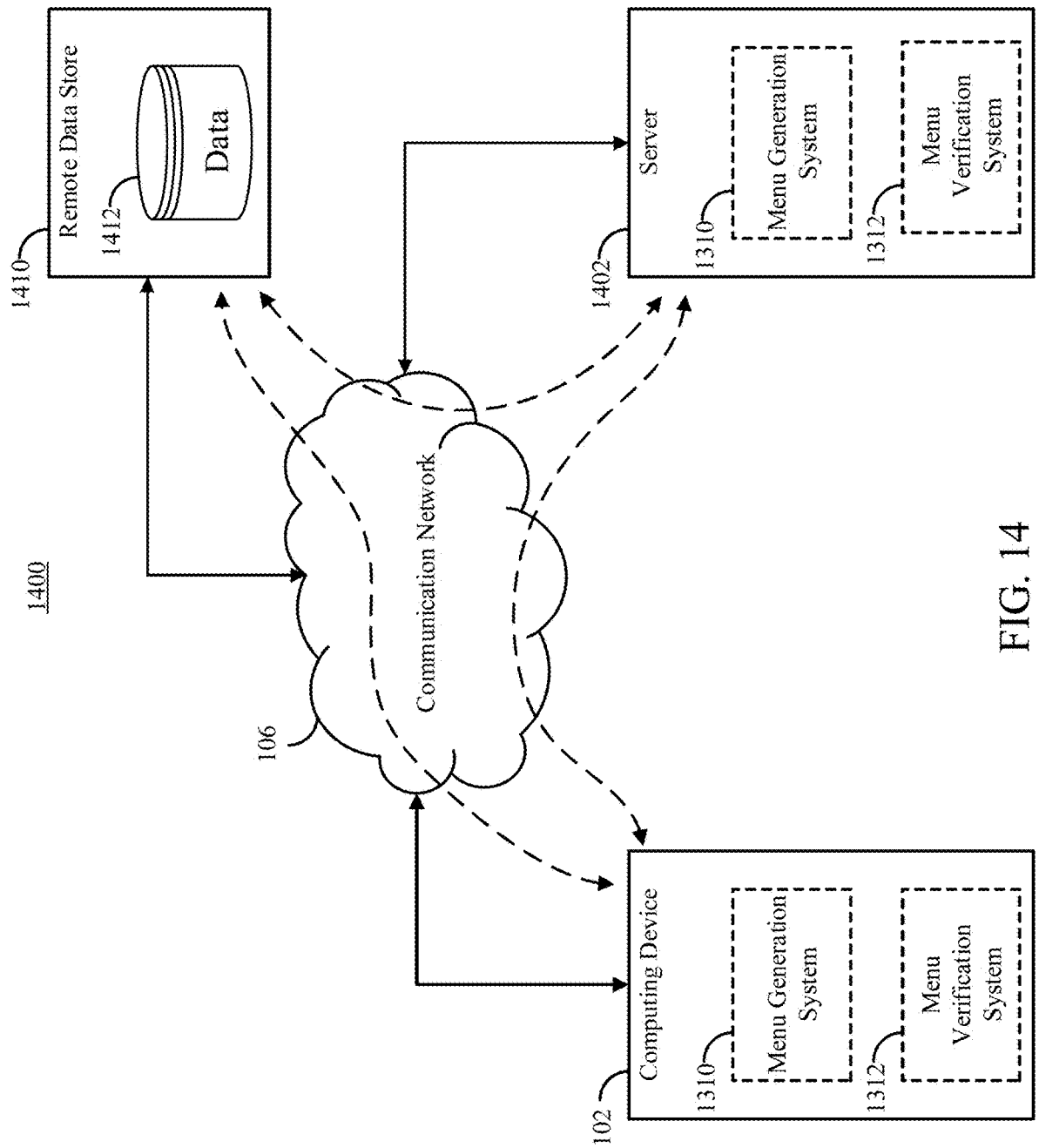
FIG. 14 shows an example of components of a system for automated dietary management in healthcare facilities in accordance with some embodiments of the disclosed subject matter.

FIG. 14 shows an example 1400 of components of a system for automated dietary management in healthcare facilities in accordance with some embodiments of the disclosed subject matter. As shown in FIG. 14, a server (or other processing unit) 1402 can execute one or more applications to provide access to menu generation system 1310 and/or menu verification system 1312. In some embodiments, menu generation system 1310 can facilitate automatic selection of recipes that can be used to prepare one or more meals that can be used as a menu for a particular facility (e.g., an elder care facility, an acute care facility, a school, and the like). In some embodiments, menu verification system 1312 can facilitate compliance of menu selections (e.g., made by menu generation system 1310 and/or a user of computing device 102) with various constraints, such as cost constraints, nutritional constraints, regulatory constraints.

In some embodiments, server 1402, menu generation system 1310, and/or a menu verification system 1312 can receive requests for information, queries, selections of items, user input, and/or any other suitable data, over communication network 106. In some embodiments, such information can be received from any suitable computing device, such as computing device 102. For example, computing device 102 can receive user input through an application being executed by computing device 102, such as through an input device (e.g., a keyboard, mouse, microphone, touchscreen, and the like). In such an example, computing device 102 can communicate information over communication network 106 to server 1402 (or another server that can provide the information to server 1402). As shown in FIG. 14, menu generation system 1310 and/or a menu verification system 1312 can be implemented using computing device 102 and/or server 1402. For example, server 1402 can be used to implement at least a portion of a back-end of menu generation system 1310 and/or a menu verification system 1312 and computing device 102 can be used to implement at least a portion of a front-end of menu generation system 1310 and/or a menu verification system 1312.

In some embodiments, server 1402 can communicate with one or more computing devices, such as a remote data store 1410 that hosts one or more databases 1412 (e.g., recipe database 1332, location database 1334, ingredient database 1336, and/or item and pricing database 1338), to collect information regarding recipes that may be appropriate for inclusion on a menu associated with a facility, information about the facility and the residents and/or patients served by the facility, information about ingredients used to prepare recipes, and information about items likely to be order by the facility. Note that, in some embodiments, database 1412 can be implemented as a distributed database and/or distributed record that is maintained across various computing devices in a network of computing devices (i.e., remote data store 1410 can include multiple computing devices in a network of computing devices). For example, in some embodiments, database 1412 can use blockchain techniques to store and update data in an encrypted and distributed record. As another example, database 1412 can be implemented as a secured and encrypted database (e.g., implemented using relational and/or non-relational data stores) to securely store and update data.

In some embodiments, server 1402 can communicate with one or more data stores 1410 to collect information that can be used to automatically generate a menu for a particular facility and/or verify that a menu is in compliance with one or more constraints (e.g., imposed by the user, a local government, a state government, the federal government). In some embodiments, computing device 102 can communicate with server 1402 to generate a menu for a particular facility. For example, computing device 102 can be used to present a user interface that can be used to initiate queries to and/or by server 1402 related to recipes to use in a menu, which facility a menu is to be generated for, information about residents and/or patients for whom a menu is to be generated, cost information associated with the facility, and any other suitable information.

In some embodiments, communications transmitted over communication network 106 and/or communication links shown in FIG. 14 can be secured using any suitable technique or combination of techniques. For example, in some embodiments, communications transmitted to and/or from server 1402, computing device 102, and/or data store 1410 can be encrypted using any suitable technique or combination of techniques. For example, communication between two or more computing devices associated with communication network 106 (e.g., server 1402, computing device 102, data store 1410, Domain Name System (DNS) servers, one or more intermediate nodes that serve as links between two or more other devices, such as switches, bridges, routers, modems, wireless access points, and the like) computing devices can be carried out based on Hypertext Transfer Protocol Secure (HTTPS). As another example, communications can be carried out based on Transport Layer Security (TLS) protocols and/or Secure Sockets Layer (SSL) protocols. As yet another example, communications can be carried out based on Internet Protocol Security (IPsec) protocols. As still another example, a virtual private network (VPN) connection can be established between one or more computing devices associated with computing network 106. In some embodiments, one or more techniques can be used to limit access to communication network 106 and/or a portion of communication network 106. For example, computing devices attempting to connect to the network and/or transmit communications using the network can be required to provide credentials (e.g., a username, a password, a hardware-based security token, a software-based security token, a one-time code, any other suitable credentials, or any suitable combination of credentials).

Figure 15:
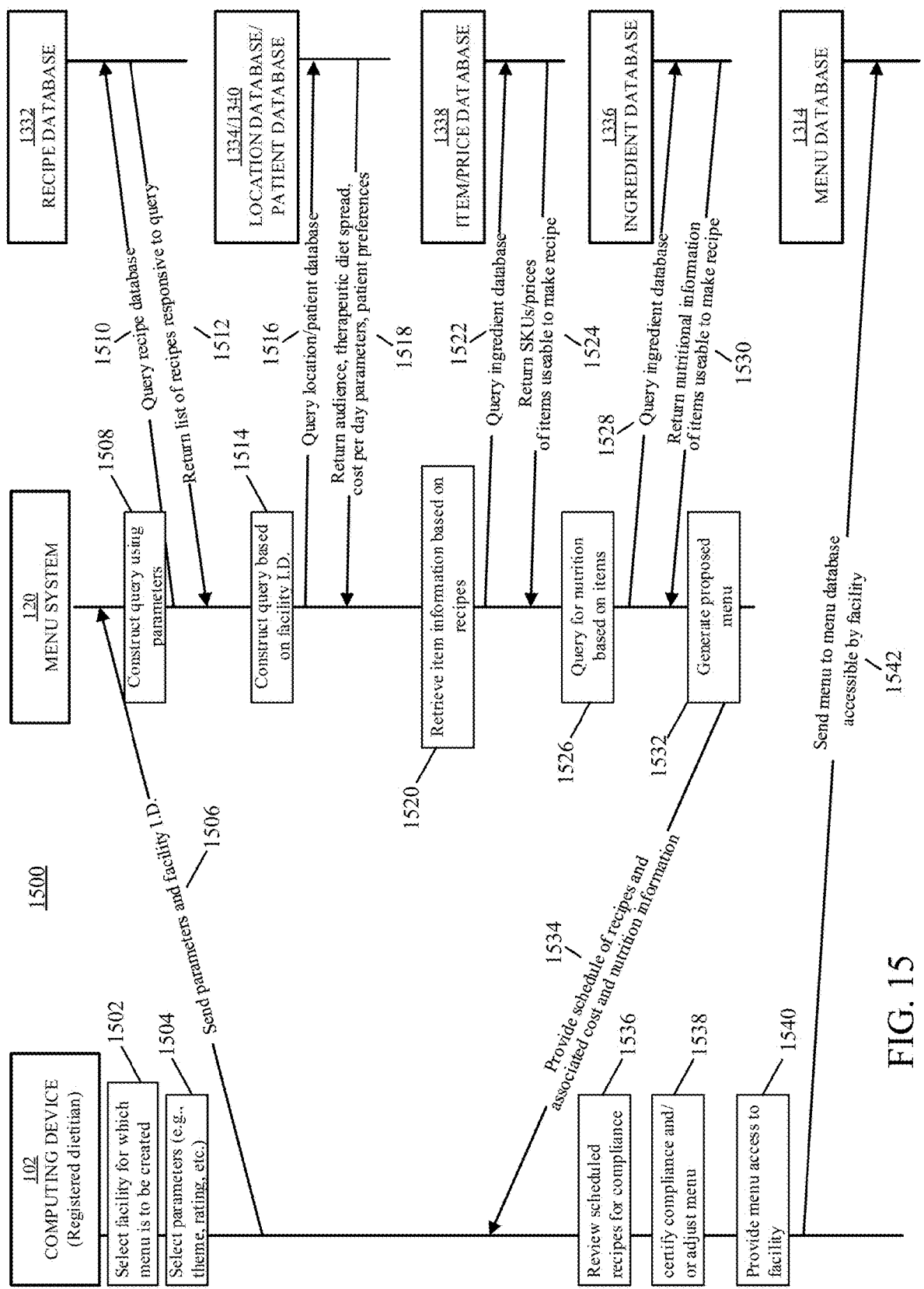
FIG. 15 shows an example of information flow among components of a system for automated dietary management in healthcare facilities in accordance with some embodiments of the disclosed subject matter.

FIG. 15 shows an example 1500 of information flow among components of a system for automated dietary management in healthcare facilities in accordance with some embodiments of the disclosed subject matter. In some embodiments, a computing device (e.g., computing device 102) can present a user interface that can be used by a registered dietitian to finalize a menu for a particular facility. At 1502, input can be received via a user interface presented by computing device 102 to select a particular facility for which a menu is to be created and/or modified. For example, the user of computing device 102 can be associated with a group of facilities, and can select a particular facility for which a menu is to be generated and/or modified. In some embodiments, the facilities with which the user of computing device 102 is associated can change over time. For example, when a particular registered dietitian is unable to oversee a particular facility (e.g., due to a vacation or other absence), the facilities associated with that registered dietitian can be redistributed to one or more other registered dietitians.

In some embodiments, the user interface presented by computing device 102 can include one or more user interface elements that can be used to select a particular facility. For example, facilities can be presented using a map user interface with selectable user interface elements mapped to represent different facilities. As another example, facilities can be presented using a list (e.g., a drop down list) that includes at least a portion of the facilities associated with the user, with each entry in the list being associated with a selectable user interface element (e.g., a radio button, a check box, a selectable link, and the like). In some embodiments, a user can select a particular facility (or group of facilities) for which to generate a menu by selecting a particular user interface element associated with the facility or facilities.

At 1504, input can be received via a user interface presented by computing device 102 to select one or more parameters that are to be used when generating a menu for the facility or facilities selected at 1502. As described above, the parameters selected can be used to express one or more preferences of what type(s) of recipes to surface. For example, parameters can be related to a theme, a rating, and so on.

At 1506, computing device 102 can communicate information about a facility and/or parameters to use in generating a menu-to-menu system 120. In some embodiments, the information can be communicated using any suitable network (e.g., communication network 106) and/or any suitable techniques. For example, the information can be encrypted at user device 102 and provided to frontend 1308 via an API.

At 1508, menu system 120 can construct queries for a recipe database based on parameters (if any) received from computing device 102 (and/or computing device 108, which can, in some embodiments, also submit queries to be used when generating a menu). In some embodiments, menu system can generate any suitable queries that can be used to surface recipes that are appropriate for inclusion in a menu for the facility identified by computing device 102.

In some embodiments, menu system 120 can generate any suitable number of queries to surface recipes that can be used to fill various spots in a menu. For example, menu system 120 can generate a query for breakfast items, a separate query for lunch items, and another query for dinner items. As another example, menu system 120 can generate a query to a first recipe database, and another for a different recipe database.

At 1510, menu system 120 can submit one or more queries to recipe database 1332 using any suitable technique or combination of techniques. In some embodiments, the query or queries can be communicated using any suitable network (e.g., communication network 106) and/or any suitable techniques. For example, the information can be encrypted at menu system 120 and sent via frontend 1308 to a frontend associated with recipe database 1332 (e.g., an API that is configured to receive, validate, and/or distribute queries).

At 1512, recipe database 1332 can return one or more results generated by the queries submitted at 110. In some embodiments, the results can be in any suitable format. For example, the results can be a list of recipes in a machine readable format (e.g., as a text file, as a spreadsheet, in a CSV format, as an XML file), a list of links to recipes, as a batch of files corresponding to recipes. In some embodiments, menu system 1514 can receive the results from recipe database 1332.

At 1514, menu system 120 can construct a query based on the facility identifying information received at 1506 that is intended to elicit information about the facility that the menu is being generated for.

At 1516, menu system 120 can send the query constructed at 1514 to location database 1334 and/or patient database 1340 as a request for information about the facility identified in the query and/or about patients at the facility. In some embodiments, the query or queries can be communicated using any suitable network (e.g., communication network 106) and/or any suitable techniques. For example, the information can be encrypted at menu system 120 and sent via frontend 1308 to a frontend associated with location database 1334 (e.g., an API that is configured to receive, validate, and/or distribute queries).

At 1518, locations database 1334 can return information about the facility in response to the query submitted at 1516. For example, locations database 1334 can return information about the number residents at the facility, the diet types that are represented and how many of each diet is represented (and if there is overlap between diets, such as a person that is associated with two diet types, such as a diabetic diet and a mechanical soft diet), and/or cost per day information.

At 1520, menu system 120 can prepare to retrieve information about which items are likely to be used to prepare each recipe. In some embodiments, menu system 120 can extract the ingredients from each recipe in preparation for identifying specific items that can serve as the ingredient and that is likely to be ordered or orderable by the facility.

At 1522, menu system 120 can send a query to item and pricing database 138 to identify one or more items that correspond to the ingredients in the recipes. In some embodiments, the query or queries can be communicated using any suitable network (e.g., communication network 106) and/or any suitable techniques. For example, the information can be encrypted at menu system 120 and sent via frontend 1308 to a frontend associated with location database 1334 (e.g., an API that is configured to receive, validate, and/or distribute queries).

In some embodiments, the query can include any suitable information (e.g., derived from the recipe) that can be used to identify a particular item that is orderable by the facility. For example, menu system 120 can use a generic name used in the recipe to identify the ingredient (e.g., chicken breast) in the query to item and pricing database 1338.

At 1524, item and pricing database 1338 can return identifying information and/or pricing information for a particular item or items that can be used as a particular ingredient when preparing a recipe. In some embodiments, the identifying information can be any suitable information such as a SKU.

At 1526, menu system 120 can use the item information (e.g., identifying information of the item) to generate queries to retrieve nutritional information for each of the items.

At 1528, menu system 120 can submit one or more queries to ingredient database 1336 using the identifying information of the items received at 1526.

At 1530, ingredient database 1336 can return nutritional information of items that are likely to be used to prepare a recipe if it is selected for inclusion in a menu.

At 1532, menu system 120 can use information gathered from various sources to generate a proposed menu. For example, menu system 120 can use recipes received from recipe database 1332, cost constraints and diet type information received from location database 1334, nutritional information received from ingredient database 1336, and pricing information received from item and pricing database 1338 to generate a menu using technique described above in connection with FIG. 13 and described below in connection with FIG. 16.

At 1534, menu system 120 can provide a schedule of recipes and associated price and nutrition information and cost information to computing device 102 for presentation to a user.

At 1536, computing device 102 can use the user interface to present menu information to the user and can prompt the user to review the proposed menu information received from menu system 120 for compliance with application regulatory and dietary constraints, and for appropriateness (e.g., that the food that has been selected is likely to be acceptable to the majority of residents and/or patients).

At 1538, computing device 102 can receive input via the user interface certifying that the menu (or a portion of the menu) is compliant and/or making one or more adjustments to the menu, which can involve swapping selected recipes for alternate recipes, or requesting new recipes as replacements for recipes that were not compliant and/or were otherwise unsuitable for inclusion in the menu.

At 1540, computing device 102 can receive input via the user interface indicating that the menu can be published to the facility for review by facility staff, for use in ordering items to prepare the meals in the menu, and/or during the course of meal preparation.

At 1542, computing device 102 can send the certified menu-to-menu database 1314 that is accessible by one or more users associated with the facility. In some embodiments, a user associated with the facility can retrieve the menu information (e.g., using computing device 108), and can review the menu and supply feedback to the user that approved the menu which can be used to make further changes before the menu is put into production and used for ordering and meal preparation.

Figure 16:
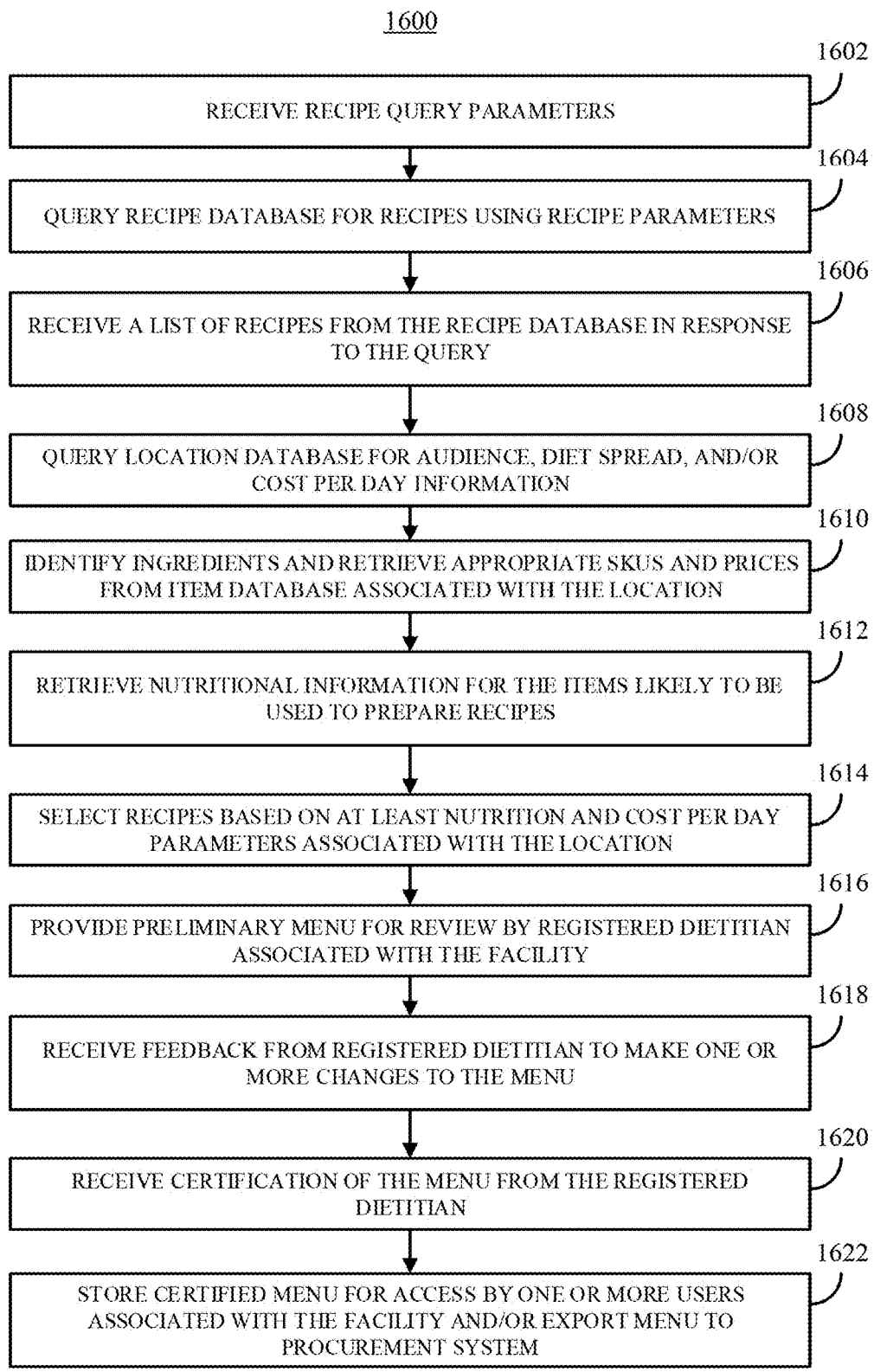
FIG. 16 shows an example of a process for automated dietary management in healthcare facilities in accordance with some embodiments of the disclosed subject matter.

FIG. 16 shows an example 1600 of a process for automated dietary management in healthcare facilities in accordance with some embodiments of the disclosed subject matter. At 1602, process 1600 can receive query parameters to be used in retrieving recipes that can be used to generate a menu for a particular facility. In some embodiments, process 1600 can receive any suitable type of query parameters (e.g., as described above in connection with FIG. 13) from any suitable source (e.g., a registered dietitian, an employee at a facility, an employee of the organization that operates the facility).

At 1604, process 1600 can query a recipe database or recipe databases using the query parameters received at 1602 and/or any other suitable parameters. In some embodiments, process 1600 can submit any suitable number of queries to the recipe database or databases to accumulate a number of recipes that is sufficient to generate a menu. For example, process 1600 can submit a first query or queries for breakfast foods, and other queries for other meals. As another example, process 1600 can submit a first query for a general diet, and other queries for recipes that are likely to comply with one or more diet types.

At 1606, process 1600 can receive recipes (e.g., as a list, or in another format or data structure) from the recipe database in response to the query submitted at 1604.

At 1608, process 1600 can query a location database for audience information (e.g., number of people, preferences), diet spread (e.g., the number of people prescribed various types of diet), and/or cost constraint information (e.g., a maximum cost per person per day, a maximum daily cost) associated with the facility for which a menu is being created.

At 1610, process 1600 can identify ingredients in the recipes and can retrieve from an item database identifying information (e.g., SKUs) of items corresponding to the ingredients. In some embodiments, process 1600 can retrieve pricing information at 1610. In some embodiments, the SKUs (or other identifying information) can identify items that are likely to be used by a facility to prepare a recipe that calls for the ingredient corresponding to the particular item. In some embodiments, such likely items can be identified using any suitable technique or combination of techniques. For example, the items can be items that are included in a facility order associated with the facility. As another example, the items can be items that the facility has ordered in the past.

At 1612, process 1600 can retrieve nutritional information for the items from an ingredient database. In some embodiments, process 1600 can retrieve nutritional information using identifying information of the items. For example, process 1600 can submit the SKUs of the items, and can receive nutritional information for an item with a matching SKU.

At 1614, process 1600 can select one or more of the recipes received from the recipe database for inclusion in a menu for the facility based on nutrition information and cost information. In some embodiments, process 1600 can use any suitable technique or combination of technique to select recipes. For example, process 1600 can use a model (e.g., a trained machine learning model, an algorithm-based optimizer model) to select recipes that satisfy one or more constraints, and that are likely to be enjoyed by the residents and/or patients of the facility for which a menu is being generated.

In some embodiments, prior to selecting a recipe, the cost and nutritional of food prepared using the recipe can be calculated and used when selecting recipes for inclusion in the menu.

In some embodiments, prior to, during, and/or after selection of recipes, process 1600 can determine whether the recipes comply with one or more constraints (e.g. as described above in connection with menu verification system 1312). In such embodiments, compliance can be determined at any suitable point, and non-compliant selections can be adjusted until a suitable menu is selected from the recipes received from the recipe database (if possible). In some embodiments, an initial menu can be generated while a user is interfacing with the system (e.g., the menu can be generated as an online process).

At 1616, process 1600 can provide a preliminary menu for review by a registered dietitian associated with the facility. In some embodiments, the preliminary menu can be presented to the registered dietitian via a user interface.

At 1618, process 1600 can receive feedback from the registered dietitian to make one or more changes to the preliminary amendment that was provided at 1616. For example, the registered dietitian can make one or more adjustments to the menu, such as swapping in an alternative in place of a recipe that was proposed by process 1600.

In some embodiments, the feedback received at 1618 can be used to adjust the menu, and present updated information to the registered dietitian about the consequences of an adjustment and/or the compliance of an adjustment. For example, after a registered dietitian provides feedback indicating that a different recipe is to be used in a particular meal, process 1600 can recalculate a cost using that recipe, and can indicate whether the cost has exceeded a maximum cost.

In some embodiments, information identifying changes made to the menu based on feedback from the registered dietitian can be saved for use in evaluation of the registered dietitian, training of a machine learning model to refine the selections made by the machine learning model to improve performance by the machine learning model, and/or updating an algorithm-based optimizer model to refine the selections made by the machine learning model to improve performance by the algorithm-based optimizer model.

At 1620, process 1600 can receive a certification of the menu from the registered dietitian indicating that the registered dietitian has confirmed that the menu is appropriate for the residents of the facility.

At 1622, process 1600 can store the certified menu for access by one or more users associated with the facility and/or can export the menu to a procurement system to be used during an ordering process.

Figure 17:
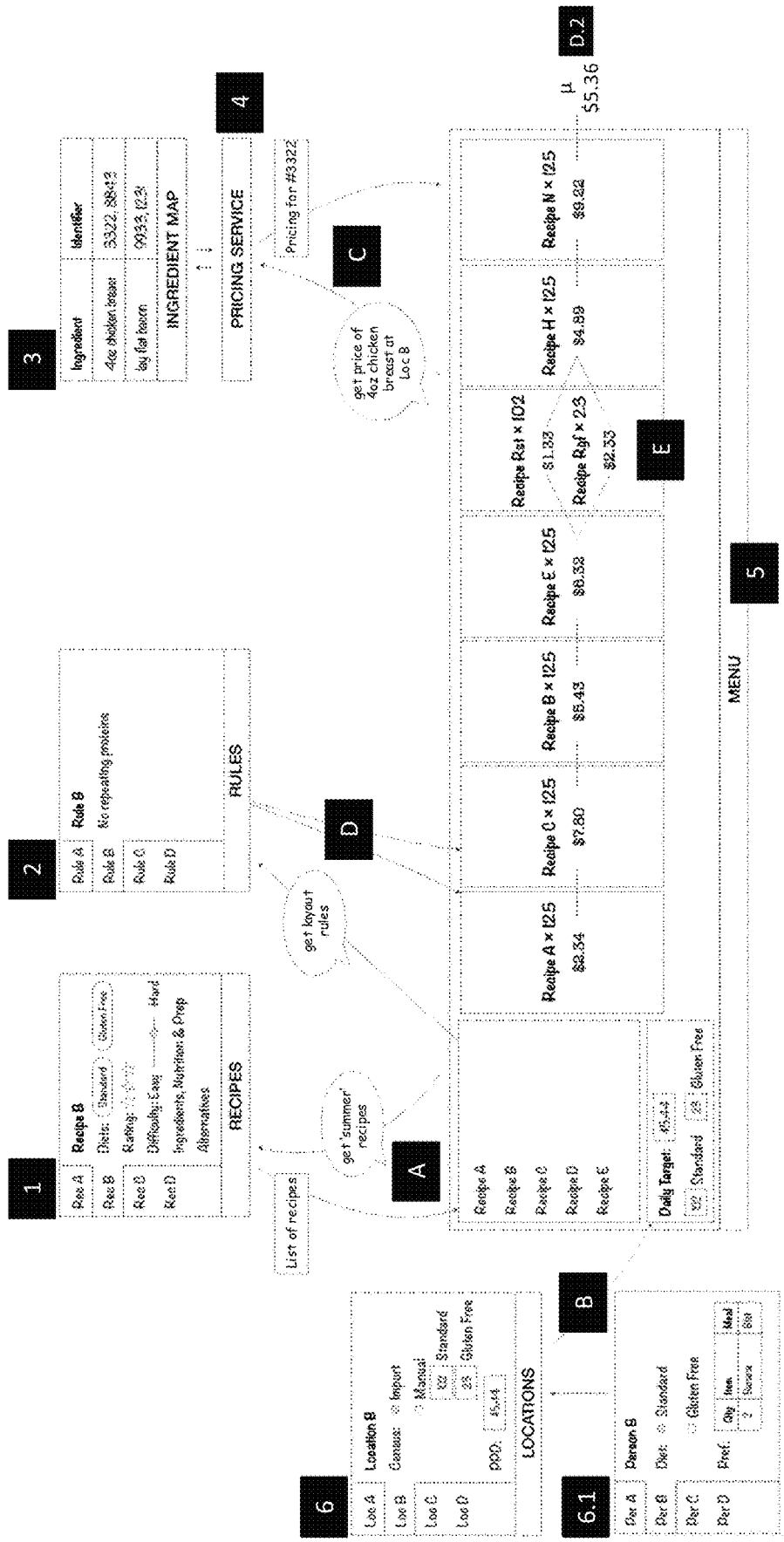
FIG. 17 shows an example of information used by a system for automated dietary management in healthcare facilities to automatically generate a menu in accordance with some embodiments of the disclosed subject matter.

FIG. 17 shows an example 1700 of information used by a system for automated dietary management in healthcare facilities to automatically generate a menu in accordance with some embodiments of the disclosed subject matter. As shown in FIG. 17, at "A," a menu system can request a list of recipes with a "summer" theme, and a recipe database can return a list of recipes "1" that meet that constraint. At "B" the menu system can use location information "6" to determine a daily target budget, and a diet spread (in this case, an average of $5.44 per day per person, and a diet spread of 102 standard and 23 gluten free). At "C" the menu system can submit a request for price information for a 4 oz chicken breast that is available at Loc B for which a menu is being constructed to a price service "4," which can retrieve the price information from an ingredient map "3." The menu system can also receive a list of menu layout rules "2" at "D," that include a rule that specifies no repeating proteins. The menu system "5" can add a meal using multiple recipes "E" where the standard recipe does not meet the specifications for all of the diets present at the facility. The information about the location from which the location information "6" is retrieved can be assembled from information about multiple individual people "6.1." In some embodiments, the menu system can determine that the average price "D.2" of $5.36 meets the average price per day criteria for the location.

FIG. 18 shows an example of a portion of a user interface for presenting patients needing attention in accordance with some embodiments of the disclosed subject matter. As shown in FIG. 18, a user can be presented with a user interface with recommendations (e.g., based on one or more factors evaluated by a model, such as a trained machine learning model) of restrictions to apply to, or remove from, particular patients needing attention. In some embodiments, when the model has high confidence that the patient would benefit from applying or removing a restriction, a user interface element that would cause the restriction to be associated (or no longer associated if the recommendation is to remove the restriction) with the patient can be pre-selected, whereas if the model has less confidence that the patient would benefit the recommendation can be presented without pre-selecting the user interface element. As shown in FIG. 18, a user interface element (shown as a hyperlink using the text "view chart") can be provided that allows the user to review pertinent information associated with each patient to make an individualized determination of what is most appropriate for that patient. When the user has verified that the restrictions to be associated with each patient are appropriate, the user can apply the selected restrictions and/or remove restrictions by selecting a user interface element (in FIG. 18 labeled "Apply Recommendations").

FIG. 19 shows an example of a portion of a user interface for presenting a facility summary in accordance with some embodiment of the disclosed subject matter. As shown in FIG. 19, the facility summary can include a summary of the various types of diets that have been assigned to patients at the facility, how many patients are requesting alternatives to the main menu, and other pertinent information.

FIG. 20 shows an example of a portion of a user interface for a summary of patient statuses across facilities in accordance with some embodiment of the disclosed subject matter. As shown in FIG. 20, a user can be presented with a user interface that the user can interact with to review the recommendations for each patient in every facility for which the user has responsibility. The summary can allow the user to quickly identify any patients that may need immediate attention, and any patients that may benefit from a consult to determine whether a change in diet would be beneficial.

It should be noted that, as used herein, the term mechanism can encompass hardware, software, firmware, or any suitable combination thereof.

It should be understood that the above described steps of the processes of FIGS. 9-12 and 15-17, can be executed or performed in any suitable order or sequence not limited to the order and sequence shown and described in the figures. Also, some of the above steps of the processes of FIGS. 9-12 and 15-17 can be executed or performed substantially simultaneously where appropriate or in parallel to reduce latency and processing times.

Although the invention has been described and illustrated in the foregoing illustrative embodiments, it is understood that the present disclosure has been made only by way of example, and that numerous changes in the details of implementation of the invention can be made without departing from the spirit and scope of the invention, which is limited only by the claims that follow. Features of the disclosed embodiments can be combined and rearranged in various ways.

What is claimed is:

1. A method for generating a medical nutrition therapy diet for a patient in a facility, the method comprising:

receiving, from a remote first computing device associated with a particular registered dietitian over a communication network, a request for identifying information associated with one or more patients associated with the facility requiring development of a medical nutrition therapy diet;

in response to the request for identifying information associated with one or more patients requiring development of a medical nutrition therapy diet, causing the first computing device to present, via a user interface, identifying information associated with a plurality of patients requiring development of a medical nutrition therapy diet;

receiving, from the first computing device, a request to present patient data associated with a first patient of the plurality of patients;

retrieving, from a second computing device over the communication network, at least a portion of nutrition data associated with the first patient, including at least one previous medical nutrition therapy diet assigned with the first patient, and data indicative of a dietary restriction associated with the first patient;

causing the first computing device to present, via the user interface, the at least one previous medical nutrition therapy diet;

causing the first computing device to present, via the user interface, at least a portion of the data indicative of the dietary restriction associated with the first patient;

prompting, via the user interface presented by the first computing device, the particular registered dietitian to review the at least one previous medical nutrition therapy diet, and the data indicative of the dietary restriction associated with the first patient;

receiving, from the first computing device based on input provided via the user interface, updated dietary restriction information comprising instructions to assign the first patient to a first diet type;

causing a model to identify a plurality of food item options available for the first patient based on the first diet type;

causing the first computing device to present, via the user interface, at least a subset of the plurality of food item options available for the first patient based on the plurality of items identified by the model that satisfy one or more conditions associated with the first diet type and that correspond to ingredients stocked by the facility;

causing the first computing device to present, via the user interface, nutritional information associated with at least the subset of the plurality of food items options including a first item and a second item;

receiving, from the first computing device, a request to add a first item of the plurality of items to the medical nutrition therapy diet;

receiving, from the first computing device, a request to add a second item of the plurality of items to the medical nutrition therapy diet;

causing the first computing device to present, via the user interface, nutritional information associated with the first item and the second item;

prompting, via the user interface presented by the first computing device, the particular registered dietitian to confirm that the medical nutrition therapy diet comprising the first item and the second item satisfies the first patient's updated dietary restrictions including requirements associated with the first diet type;

receiving, from the first computing device, an indication that input was received via the user interface confirming that the medical nutrition therapy diet satisfies the first patient's updated dietary restrictions;

in response to receiving confirmation that the medical nutrition therapy diet satisfies the first patient's updated dietary restrictions, recording an indication that the particular registered dietitian approved the medical nutrition therapy diet as satisfying the first patient's updated dietary restrictions;

causing the medical nutrition therapy diet to be transmitted to a food service system to cause one or more meals to be prepared for the first patient at the facility based on the medical nutrition therapy diet;

receiving outcome data comprising measurable physiological data that is indicative of the first patient's response to the medical nutrition therapy diet;

generating training data for the model using the medical nutrition therapy diet and the outcome data; and providing the training data to a third computing device associated with the model such that the model can be updated using the training data.

2. The method of claim 1, further comprising associating each of the plurality of patients with the facility based on at least one of identifying information associated with the patient and metadata associated with the patient.

3. The method of claim 1, further comprising:
receiving identifying information associated with the particular registered dietitian; and
receiving a request to associate the particular registered dietitian with an organization that operates the facility.

4. The method of claim 3, further comprising:
receiving facility privileges information indicating that the particular registered dietitian has been granted privileges to practice at the facility;
receiving licensing information indicating one or more jurisdictions in which the particular registered dietitian is licensed to practice; and
causing the facility privileges information and the licensing information to be stored in a data store.

5. The method of claim 4, further comprising:
determining, based on the stored licensing information, that the particular registered dietitian is licensed to practice in a jurisdiction that requires licensure; and
causing the first computing device to present, via the user interface, a user interface element that conveys information indicative of the particular registered dietitian being permitted to develop the medical nutrition therapy diet for the first patient.

6. The method of claim 5, further comprising:
determining, based on the stored facility privileges information, that the particular registered dietitian has been granted privileges to practice in the facility; and
in response to determining that the particular registered dietitian has been granted privileges to practice in the facility, causing the first computing device to present, via the user interface, the user interface element.

7. The method of claim 1, further comprising:
causing the first computing device to present, via the user interface, a plurality of user interface elements corresponding to the subset of the plurality of food item options that convey a recommended medical nutrition therapy diet for the first patient selected by the model.

8. The method of claim 7, wherein the model is a trained machine learning model that was trained to select food items that comply with one or more nutrition restrictions, including food preparation restrictions, using second training data comprising past medical nutrition therapy diets associated with a multitude of patients, information indicative of a dietary restrictions for each of the multitude of patients, and outcomes for each of the multitude of patients.

9. The method of claim 1, further comprising:
receiving, from an electronic health record system, medical record data associated with the first patient; and causing the first computing device to present, via the user interface, a plurality of user interface elements that convey medical condition data for the first patient extracted from the medical record data.

10. The method of claim 9, wherein:
generating the training data comprises generating the training data using the updated dietary restriction information and associating the training data with anonymized identifying information; and
providing the training data to the third computing device comprises providing the training data and the anonymized identifying information to the third computing device such that the model can be updated using the training data while ensuring that personally identifying information of the first patient is not disseminated.

11. The method of claim 10, further comprising:
causing the model to be updated based on the training data.

12. The method of claim 10, wherein the outcome data associated with the first patient comprises data indicative of the first patient's weight at two or more points in time associated with the medical nutrition therapy diet.

13. The method of claim 10, wherein the outcome data associated with the first patient comprises data indicative of the first patient's blood glucose at two or more points in time associated with the medical nutrition therapy diet.

14. The method of claim 1, wherein retrieving at least a portion of the nutrition data associated with the first patient comprises querying a blockchain distributed ledger in which prior medical nutrition therapy diet associated with the first patient are recorded, the method further comprising:
receiving patient data associated with the first patient, the patient data comprising at least any currently existing dietary restrictions, texture restrictions, liquid restrictions, likes, dislikes, patient feedback, allergies, and physician ordered restrictions recorded in an electronic health record associated with the patient;
causing the patient data to be collected into a transaction data register;
receiving data from the first computing device that was provided as input via the user interface;
causing the data provided as input via the user interface to be collected into the transaction data register;
receiving data from the model;
causing the data received from the model to be collected into the transaction data register;
causing the transaction register data to be configured into a new blockchain distributed ledger block;
associating a cryptographic hash of a previous blockchain distributed ledger block and a timestamp with the new blockchain distributed ledger block; and
causing the new blockchain distributed ledger block to be written to the blockchain distributed ledger using the cryptographic hash.

15. A system for automatically generating a medical nutrition therapy diet for a patient in a facility, the system comprising:
at least one hardware processor that is programmed to:
receive, from a remote first computing device associated with a particular registered dietitian over a communication network, a request for identifying information associated with one or more patients associated with the facility requiring development of a medical nutrition therapy diet;
in response to the request for identifying information associated with one or more patients requiring development of a medical nutrition therapy diet, cause the first computing device to present, via a user interface, identifying information associated with a plurality of patients requiring development of a medical nutrition therapy diet;

receive, from the first computing device, a request to present patient data associated with a first patient of the plurality of patients;

retrieve, from a second computing device over the communication network, at least a portion of nutrition data associated with the first patient, including at least one previous medical nutrition therapy diet assigned with the first patient, and data indicative of a dietary restriction associated with the first patient;

causing the first computing device to present, via the user interface, the at least one previous medical nutrition therapy diet;

causing the first computing device to present, via the user interface, at least a portion of the data indicative of the dietary restriction associated with the first patient;

prompting, via the user interface presented by the first computing device, the particular registered dietitian to review the at least one previous medical nutrition therapy diet, and the data indicative of the dietary restriction associated with the first patient;

receiving, from the first computing device based on input provided via the user interface, updated dietary restriction information comprising instructions to assign the first patient to a first diet type;

causing a model to identify a plurality of food item options available for the first patient based on the first diet type;

causing the first computing device to present, via the user interface, at least a subset of the plurality of food item options available for the first patient based on the plurality of items identified by the model that satisfy one or more conditions associated with the first diet type and that correspond to ingredients stocked by the facility;

causing the first computing device to present, via the user interface, nutritional information associated with at least the subset of the plurality of food items options including a first item and a second item;

receiving, from the first computing device, a request to add a first item of the plurality of items to the medical nutrition therapy diet;

receiving, from the first computing device, a request to add a second item of the plurality of items to the medical nutrition therapy diet;

causing the first computing device to present, via the user interface, nutritional information associated with the first item and the second item;

prompting, via the user interface presented by the first computing device, the particular registered dietitian to confirm that the medical nutrition therapy diet comprising the first item and the second item satisfies the first patient's updated dietary restrictions including requirements associated with the first diet type;

receiving, from the first computing device, an indication that input was received via the user interface confirming that the medical nutrition therapy diet satisfies the first patient's updated dietary restrictions;

in response to receiving confirmation that the medical nutrition therapy diet satisfies the first patient's updated dietary restrictions, recording an indication that the particular registered dietitian approved the medical nutrition therapy diet as satisfying the first patient's updated dietary restrictions;

causing the medical nutrition therapy diet to be transmitted to a food service system to cause one or more meals to be prepared for the first patient at the facility based on the medical nutrition therapy diet;

receiving outcome data comprising measurable physiological data that is indicative of the first patient's response to the medical nutrition therapy diet;

generating training data for the model using the medical nutrition therapy diet and the outcome data; and providing the training data to a third computing device associated with the model such that the model can be updated using the training data.

16. The system of claim 15, further comprising:

a licensing database comprising information related to licensing requirements for registered dietitian in a plurality of jurisdictions indicating which of the plurality of jurisdictions require a license, and which of the plurality of jurisdictions grant reciprocity to dietitians licensed in particular other jurisdictions;

wherein the at least one hardware processor that is further programmed to:
submit a query to the licensing database for licensing requirements of a first jurisdiction;
receive, from the licensing database, licensing requirements of the first jurisdiction; and
determine that the particular registered dietitian is legally permitted to practice in the first jurisdiction based on the licensing requirements of the first jurisdiction and licensing information associated with the particular registered dietitian.

17. The system of claim 15, further comprising:

a privileges database comprising information identifying facilities for which each of a plurality of registered dietitians has received privileges to practice in that facility;

wherein the at least one hardware processor that is further programmed to:
submit a query to the privileges database for privileges requirements;
receive, from the privileges database, privilege information associated with the particular registered dietitian; and
determine that the particular registered dietitian has been granted privileges to practice at the facility based on the privilege information associated with the particular registered dietitian.

18. The system of claim 15, further comprising:

a food item nutrition database comprising information identifying, for each of a plurality of food items, a detailed list of ingredients, a plant where the food item was manufactured, and a production line where the food item was manufactured to identify the possibility of preparation and potential cross-contamination of the food item with an unlisted ingredient;

wherein the at least one hardware processor that is further programmed to:
submit a query to the food item nutrition database for food item nutrition information of a first food item;
receive, from the food item nutrition database, nutrition information of the first food item; and
determine that first food item satisfies one or more dietary restrictions, texture restrictions, liquid restrictions, allergen restrictions, and cross-contamination restrictions associated with the first patient based on the nutrition information of the first food item.

19. The system of claim 15, further comprising:
a health record database comprising electronic health record data;
wherein the at least one hardware processor that is further programmed to:
submit a query to the health record database for health record data associated with the first patient;
receive, from the health record database, the health record data associated with the first patient;
determine, based on the health record data associated with the first patient, that the first patient requires a medical nutrition therapy diet;
determine, based on the health record data associated with the first patient, if there is an active medical order restricting a medical nutrition therapy diet; and
determine, based on the health record data associated with the first patient, if the first patient has a health condition that requires a medical nutrition therapy diet.

20. A non-transitory computer-readable storage medium having instructions stored thereon that, when executed by processing circuitry, cause the processing circuitry to implement operations comprising:
receiving, from a remote first computing device associated with a particular registered dietitian over a communication network, a request for identifying information associated with one or more patients associated with the facility requiring development of a medical nutrition therapy diet;
in response to the request for identifying information associated with one or more patients requiring development of a medical nutrition therapy diet, causing the first computing device to present, via a user interface, identifying information associated with a plurality of patients requiring development of a medical nutrition therapy diet;
receiving, from the first computing device, a request to present patient data associated with a first patient of the plurality of patients;
retrieving, from a second computing device over the communication network, at least a portion of nutrition data associated with the first patient, including at least one previous medical nutrition therapy diet assigned with the first patient, and data indicative of a dietary restriction associated with the first patient;
causing the first computing device to present, via the user interface, the at least one previous medical nutrition therapy diet;
causing the first computing device to present, via the user interface, at least a portion of the data indicative of the dietary restriction associated with the first patient;
prompting, via the user interface presented by the first computing device, the particular registered dietitian to review the at least one previous medical nutrition therapy diet, and the data indicative of the dietary restriction associated with the first patient;
receiving, from the first computing device based on input provided via the user interface, updated dietary restriction information comprising instructions to assign the first patient to a first diet type;
causing a model to identify a plurality of food item options available for the first patient based on the first diet type;
causing the first computing device to present, via the user interface, at least a subset of the plurality of food item options available for the first patient based on the plurality of items identified by the model that satisfy one or more conditions associated with the first diet type and that correspond to ingredients stocked by the facility;
causing the first computing device to present, via the user interface, nutritional information associated with at least the subset of the plurality of food items options including a first item and a second item;
receiving, from the first computing device, a request to add a first item of the plurality of items to the medical nutrition therapy diet;
receiving, from the first computing device, a request to add a second item of the plurality of items to the medical nutrition therapy diet;
causing the first computing device to present, via the user interface, nutritional information associated with the first item and the second item;
prompting, via the user interface presented by the first computing device, the particular registered dietitian to confirm that the medical nutrition therapy diet comprising the first item and the second item satisfies the first patient's updated dietary restrictions including requirements associated with the first diet type;
receiving, from the first computing device, an indication that input was received via the user interface confirming that the medical nutrition therapy diet satisfies the first patient's updated dietary restrictions;
in response to receiving confirmation that the medical nutrition therapy diet satisfies the first patient's updated dietary restrictions, recording an indication that the particular registered dietitian approved the medical nutrition therapy diet as satisfying the first patient's updated dietary restrictions;
causing the medical nutrition therapy diet to be transmitted to a food service system to cause one or more meals to be prepared for the first patient at the facility based on the medical nutrition therapy diet;
receiving outcome data comprising measurable physiological data that is indicative of the first patient's response to the medical nutrition therapy diet;
generating training data for the model using the medical nutrition therapy diet and the outcome data; and
providing the training data to a third computing device associated with the model such that the model can be updated using the training data.

* * * * *